United States Patent [19]

Rajadhyaksha

[11] Patent Number: 4,960,771

[45] Date of Patent: Oct. 2, 1990

[54] OXAZOLIDINONE PENETRATION ENHANCING COMPOUNDS

[76] Inventor: Vithal J. Rajadhyaksha, 27436 Esquina, Mission Viejo, Calif. 92691

[21] Appl. No.: 218,316

[22] Filed: Jul. 12, 1988

[51] Int. Cl.$^5$ .................... A61K 31/42; A61K 31/535
[52] U.S. Cl. .................. 514/228.8; 514/376; 514/452; 514/467; 514/470; 514/947
[58] Field of Search ................. 514/376, 947, 228.8, 514/452, 467

[56] References Cited

U.S. PATENT DOCUMENTS

| | | | |
|---|---|---|---|
| 2,909,467 | 10/1959 | Shapiro | 514/376 |
| 4,405,616 | 9/1983 | Rajadhyaksha | 514/947 X |
| 4,423,040 | 12/1983 | Rajadhyaksha | 514/947 X |
| 4,594,243 | 6/1986 | Satoh et al. | 424/78 |

OTHER PUBLICATIONS

Catalog Handbook of Fine Chemicals 1988–1989, p. 609, Aldrich Chemical Company, Milwaukee, Wisconsin.
Stoughton et al., pp. 737–739, Development Drug and Industrial Pharmacy, 9(4), 725–744 (1983).
Woodford and Barry, pp. 170–172, J. Toxicol.-Cut. & Ocular Toxicol. 5(3), 167–177 (1986).
Gummer, P. 566 in Percutaneous Absorption Mechanism-Methodolgy—Drug Delivery, Ed. Bronaugh and Maibach, chapter 43, 561–571, Marcel Dekker, 1985.
Transdermal Delivery of Drugs, p. 76, vol. II, Ed. Kydonieus and Berner, CRC Press Inc., Boca Raton, Florida, 1987.
Barry in Dermatological Formulations, Barry, pp. 160–172, Marcel Dekker, New York, 1983.

*Primary Examiner*—Leonard Schenkman
*Attorney, Agent, or Firm*—Grant L. Hubbard

[57] ABSTRACT

Compositions for carrying physiologically active agents through body membranes having the structural formula I:

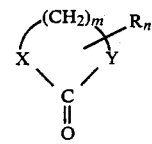

where:
R=H, Alkyl group containing from 1–18 carbon atoms, cycloalkyl, aryl, aralkyl, alkoxy, hydroxyalkyl, alkoyloxyalkyl, acyloxyalkyl and alkoxyalkyl;
X=O and NR$_1$, where R$_1$ is selected from H, alkyl, aralkyl acyl group containing from 1–18 carbon atoms, cycloalkyl, hydroxyalkyl, alkoyloxyalkyl acyloxyalkyl and alkoxyalkyl;
Y=O and NR$_2$, where R$_2$ is selected from H, alkyl, aralkyl, cycloalkyl, acyl group containing from 1–18 carbon atoms, hydroxyalkyl, alkoyloxyalkyl, acyloxyalkyl and alkoxyalkyl;
m=2–4; and
n=0–4,
are disclosed.

8 Claims, No Drawings

OXAZOLIDINONE PENETRATION ENHANCING COMPOUNDS

FIELD OF THE INVENTION

This invention relates to pharmaceutical and biological penetration enhancing compounds.

BACKGROUND OF THE INVENTION

Many physiologically active agents are best applied topically to obtain desirable results. Topical application, in the form of creams, lotions, gels, solutions, etc., largely avoids side effects of the agents and permits high level concentrations of the agents.

Some therapeutic drugs may also be administered for systemic use through the skin or other body membranes including intranasal and intravaginal application of humans and other animals, utilizing a transdermal device or formulated in a suppository or aerosol spray. For some years, pharmaceutical researchers have sought an affective means of introducing drugs into the bloodstream by applying them to the unbroken skin. Among other advantages, such administration can provide a comfortable, convenient and safe way of giving many drugs now taken orally or infused into veins or injected intramuscularly.

Using skin as the portal for drug entry offers unique potential because transdermal delivery permits close control over drug absorption. For example, it avoids factors that can cause unpredictable absorption from the gastrointestinal tract including changes in acidity, motility, and food content. It also avoids initial metabolism of the drug by the liver known as the first pass effect. Thus, sustained drug delivery through the skin can achieve a high degree of control over blood concentrations of drugs.

Close control over drug concentration in blood can translate readily into safer and more comfortable treatment. When a drug's adverse effects occur at higher concentrations than its beneficial ones, rate control can maintain the concentration that evoke only—or principally the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal systems that require application infrequently—in some cases, only once or twice weekly—and reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, those susceptible to a higher first pass liver metabolism, or those requiring frequent dosing in oral or injectable form.

Transdermal therapy permits a much wider use of natural substances such as hormones. Often the survival times of these substances in the body are so short that they would have to be taken many times daily in ordinary dosage forms. Sustained transdermal delivery not only provides a practical way of administering these substances but also potentiates their ability to mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of the drug to the circulation over prolonged periods of time to obtain uniform delivery rate and maintain blood levels of the drug. Commencement and termination of drug therapy is initiated by the application and removal of the dosing devices from the skin. Uncertainties of administration through the gastrointestinal tract and the inconvenience of administration by injection are eliminated. Since a high concentration of the drug never enters the body, problems of pulse entry are overcome and metabolic half-life is not a factor of controlling importance.

The greatest problem in applying physiologically active agents topically or transdermally is that the skin is an effective barrier to penetration. The epidermis of the skin has an exterior layer of dead cells called the stratum corneum which is tightly compacted and oily, and which provides an effective barrier against gaseous, solid or liquid chemical agents, whether used alone or in water or in oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use of treating such conditions as inflammation, acne, psoriasis, herpes labialis, herpes genitalis, eczema, infections caused by fungi, viruses and other microorganisms, or other disorders or conditions of the skin or mucous membranes, or of conditions beneath the exterior surface of the skin or mucous membranes. The stratum corneum also prevents the skin from absorbing and retaining cosmetic-type materials such as sunscreens, perfumes, mosquito repellents and the like.

Physiologically active agents may be applied to the locally affected parts of the body in the form of a solution, cream, lotion or gel utilizing the vehicle system described herein. These agents may also be delivered for systemic use utilizing the vehicle system in a transdermal patch. Vehicles such as USP cold cream, ethanol and various ointments, oils, solvents and emulsions have been used heretofore to apply physiologically active ingredients locally. Most such vehicles are not effective to carry significant amounts of physiologically active agents into and through the skin. One such vehicle is dimethyl sulfoxide, which is described in U.S. Pat. No. 3,551,554.

My previous inventions disclosed in U.S. Pat. Nos. 3,989,816; 3,991,203; 4,122,170; 4,316,893; 4,415,563; 4,423,040; 4,424,210; 4,444,762 describe a method for enhancing the topical administration of physiologically active agents by combining such an agent with an effective amount of a penetration enhancer and applying the combination topically to humans or animals, in the form of a solution, cream, gel, lotion, etc. This prior art discloses N-alkyl substituted cyclic lactams as penetration enhancers.

My related U.S. Pat. No. 4,405,616 describes a method for administering systemically active agents through the skin or other body membranes of humans and animals, utilizing a transdermal device or formulation containing an effective amount of a suitable membrane penetration enhancer selected from the disclosed N-alkyl substituted cyclic lactams.

My related U.S. application, Ser. No. 783,621, filed on Sept. 30, 1985, describes a method for enhancing topical and transdermal administration of physiologically active agents with membrane penetration enhancers selected from the alkanoic acid cyclic amides disclosed therein.

My related U.S. application, Ser. No. 002,387, filed on Jan. 12, 1987, describes a method for enhancing topical and transdermal administration of physiologically active agents with membrane penetration enhancers selected from heterocyclic compounds containing two heteroatoms.

Penetration enhancers for enhancing systemic administration of therapeutic agents transdermally disclosed in the art include dodecyl pyrrolidone, dimethyl lauramide and dimethyl sulfoxide. These agents may be used prior to or concurrently with the administration of the active agent, see, e.g., U.S. Pat. Nos. 4,031,894; 3,996,934 and 3,921,636.

SUMMARY OF THE INVENTION

The invention relates to compositions for carrying physiologically active agents through body membranes such as skin, for retaining these agents in body tissues, and to a method of administering systemically active agents through the skin or other body membranes of humans and animals, utilizing a transdermal device or formulation, containing an effective, non-toxic amount of a membrane penetration enhancer having the structural formula I:

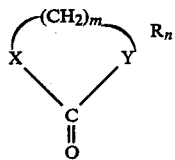

where:
R=H, Alkyl group containing from 1-18 carbon atoms, cycloalkyl, aryl, aralkyl, alkoxy, hydroxyalkyl, alkoyloxyalkyl, acyloxyalkyl and alkoxyalkyl;
X=O and $NR_1$, where $R_1$ is selected from H, alkyl, aralkyl, acyl group containing from 1-18 carbon atoms, cycloalkyl, hydroxyalkyl, alkoyloxyalkyl acyloxyalkyl and alkoxyalkyl;
Y=O and $NR_2$, where $R_2$ is selected from H, alkyl, aralkyl, cycloalkyl, acyl group containing from 1-18 carbon atoms, hydroxyalkyl, alkoyloxyalkyl, acyloxyalkyl and alkoxyalkyl;
m=2-4; and
n=0-4;
with the provisos that:
(i) when R=H, X=$NR_1$, and Y=$NR_2$ then $R_1$ and $R_2$ are not alkyl;
(ii) when R=H, X=O and Y=$NR_2$, then R is not alkyl; and
(iii) when X and Y are O, then R is not lower alkyl, i.e., if alkyl, R is C5-C18.

The alkyl, cycloalkyl, acyl, aralkyl, hydroxyalkyl, alkoyloxyalkyl, acyloxyalkyl and alkoxyalkyl groups may be straight or branched, and may also include several unsaturated linkages and chiral centers. Two R substituents may combine to form a cyclic ring containing up to 12 carbon atoms.

In one preferred embodiment of I, R is alkyl group containing from 5-18 carbon atoms, aryl, aralkyl, cycloalkyl, alkoxy, hydroxyalkyl, alkoyloxyalkyl, acyloxyalkyl and alkoxyalkyl. Y is $NR_2$ where $R_2$ is H, lower alkyl, lower acyl, aralkyl, hydroxyalkyl, alkoyloxyalkyl, acyloxyalkyl and alkoxyalkyl, X is O and m and n being as defined above.

In another preferred embodiment of the composition I, R is H, lower alkyl, aryl, lower aralkyl, cycloalkyl, alkoxy, hydroxyalkyl, alkoyloxyalkyl, acyloxyalkyl and alkoxyalkyl, Y is $NR_2$, where $R_2$ is an acyl group with from 1-18 carbon atoms, aralkyl, cycloalkyl, hydroxyalkyl, alkoyloxyalkyl, acyloxyalkyl and alkoxyalkyl, X is O, and m and n being as defined above.

In another preferred embodiment of I, R is H, an alkyl group containing from 1-18 carbon atoms, aryl, aralkyl, cycloalkyl, alkoxy, hydroxyalkyl, alkoyloxyalkyl, acyloxyalkyl and alkoxyalkyl, Y is $NR_2$, where $R_1$ is H, alkyl, aralkyl, cycloalkyl, lower acyl, hydroxyalkyl, alkoyloxyalkyl, acyloxyalkyl and alkoxyalkyl, X is $NR_1$ and m, n and $R_1$ being as defined above, with the proviso that when R is H, then $R_1$ and $R_2$ are not H or alkyl.

In a third exemplary preferred embodiment of I, X and Y are O and R is C5-C18 alkyl, aryl, aralkyl, cycloalkyl, hydroxyalkyl, alkoyloxyalkyl, acyloxyalkyl and alkoxyalkyl, and m and n being as defined above. It has been found that the physiologically active agents are carried through body membranes by the claimed penetration enhancers and are retained in the body tissue when applied topically in the form of a cream, gel or lotion or absorbed systemically when applied in the form of a transdermal device or formulation, for example, as a transdermal patch, a rectal or vaginal suppository, as a nasal spray or when incorporated in a vaginal sponge or tampon.

DETAILED DESCRIPTION OF THE INVENTION

Typical examples of compounds included in the foregoing formula I of this invention are the following:
(1) 4-Decyloxazolidin-2-one.
(2) 3-Methyl-4-decyloxazolidin-2-one.
(3) 3-Acetyl-4-decyloxazolidin-2-one.
(4) 4-Benzyloxazolidin-2-one.
(5) 3-Methyl-4-benzyloxazolidin-2-one.
(6) 3-Butyl-4-benzyloxazolidin-2-one.
(7) 3-(2-Butyl)-4-benzyloxazolidin-2-one.
(8) 3-(2-Methylpropyl)-4-benzyloxazolidin-2-one.
(9) 5-Decyloxazolidin-2-one.
(10) 3-Methyl-5-decyloxazolidin-2-one.
(11) 3-Acetyl-5-decyloxazolidin-2-one.
(12) 4,4-Dimethyl-5-decyloxazolidin-2-one.
(13) 3,4,4-Trimethyl-5-decyloxazolidin-2-one.
(14) 3-Acetyl-4,4-dimethyl-5-decyloxazolidin-2-one.
(15) 4-Phenyloxazolidin-2-one.
(16) 3-Methyl-4-phenyloxazolidin-2-one.
(17) 3-Acetyl-4-phenyloxazolidin-2-one.

(18) 4-Methyl-5-phenyloxazolidin-2-one.
(19) 3,4-Dimethyl-5-phenyloxazolidin-2-one.
(20) 3-Acetyl-4-methyl-5-phenyloxazolidin-2-one.
(21) 5-Decyltetrahydro-1,3-oxazin-2-one.
(22) 3-Methyl-5-decyltetrahydro-1,3-oxazin-2-one.
(23) 3-Acetyl-5-decyltetrahydro-1,3-oxazin-2-one.
(24) 4-Dodecyltetrahydro-1,3-oxazin-2-one.
(25) 3-Methyl-4-dodecyltetrahydro-1,3-oxazin-2-one.
(26) 3-Acetyl-4-dodecyltetrahydro-1,3-oxazin-2-one.
(27) 3-(1-oxododecyl)oxazolidin-2-one.
(28) 3-(1-oxododecyl)-4-methyloxazolidin-2-one.
(29) 3-(1-oxododecyl)-5-methyloxazolidin-2-one.
(30) 3-(1-oxododecyl)-4,4-dimethyloxazolidin-2-one.
(31) 3-(1-oxodecyl)-4-(2-propyl)oxazolidin-2-one.
(32) 3-(1-oxodecyl)-4-(2-butyl)oxazolidin-2-one.
(33) 3-(1-oxodecyl)-4-benzyloxazolidin-2-one.
(34) 3-(I-oxooctadec-9-enyl)oxazolidin-2-one.
(35) 3-(1-oxooctadec-9-enyl)-4,4-dimethyloxazolidin-2-one.
(36) 3-(1-oxododecyl)tetrahydro-1,3-oxazin-2-one.
(37) 4-Undecylimidazolidin-2-one.
(38) 1,3-Dimethyl-4-undecylimidazolidin-2-one.
(39) 1-Methyl-5-dodecylimidazolidin-2-one.
(40) 1-Methyl-3-acetyl-5-dodecylimidazolidin-2-one.
(41) Bis-1,3-(1-oxohexyl)imidazolidin-2-one.
(42) 1,3-diacetyl-4-dodecylimidazolidin-2-one.
(43) 5-Dodecyltetrahydropyrimidin-2-one.
(44) 1,3-Dimethyl-5-dodecyltetrahydropyrimidin-2-one.
(45) 1,3-Diacetyl-5-dodecyltetrahydropyrimidin-2- one.
(46) Bis-1,3-(1-oxohexyl)tetrahydropyrimidin-2-one.
(47) 3-(2-Hydroxyethyl)-4-decyloxazolidin-2-one.
(48) 3-(2-Ethoxyethyl)-4-decyloxazolidin-2-one.
(49) 1-(2-Hydroxyethyl)-3-dodecylimidazolidin-2-one.
(50) 1-(2-hydroxyethyl)-3-octylimidazolidin-2-one.
(51) 1,3-bis-(2-butoxyethyl)imidazolidin-2-one.
(52) 1-(3-ethoxypropyl)-3-(2-methoxyethyl)imidazolidin-2-one.
(53) 3-(3-ethoxypropyl)oxazolidin-2-one.
(54) 3-(2-octyloxyethyl)oxazolidin-2-one.
(55) 1-butyl-3-(2-ethoxyethyl)imidazolidin-2-one.
(56) 1-butyl-3-(2-butoxyethyl)imidazolidin-2-one.
(57) 4,5-dibutoxy-1,3-dimethylimidazolidin-2-one.
(58) 4,5-diethoxy-1-butyl-3-propylimidazolidin-2- one.
(59) 4,5-diethoxy-1-octyl-3-propylimidazolidin-2-one.
(60) 4,5-diisopropoxy-1-butyl-3-propylimidazolidin-2-one.
(61) 4,5-dioctyloxy-1,3-dimethylimidazolidin-2-one.
(62) 4,5-dioctyloxyimidazolidin-2-one.
(63) 3-(2-oxazolidonyl) ethyl dodecanoate
(64) 5-(octyloxy methyl) oxazolidin-2-one.
(65) 3-methyl-5-(hexyloxy methyl) oxazolidin-2-one.
(66) 3-methyl-5-(octanoyloxy) oxazolidin-2-one.
(67) 4-methyl-4-(octyloxymethyl) oxazolidin-2-one.
(68) 4-(dodecanoyloxymethyl)-4-methyloxazolidin-2-one.
(69) 4-decyl-1,3-dioxolan-2-one.
(70) 4-decyloxymethyl-1,3-dioxolan-2-one.
(71) 4-[(octadec-9-enoyloxy) methyl]-1,3-dioxolan-2-one.

The following oxazolidin-2-ones and tetrahydro-1,3-oxazin-2-ones, encompassed by general formula I of this invention are known.

Chemical Abstracts, Collective Volumes 1 through 11 and Volumes 106-107 (up to 1987) disclose the following oxazolidin-2-ones: 3-methyl; 3-ethyl; 3-propyl; 3-isopropyl; 3-butyl; 3-isobutyl; 3-tertbutyl; 3-pentyl; 3-isopentyl; 3-hexyl; 3-octyl; 3-nonyl; 3-dodecyl; 3-cyclohexyl; 3-vinyl; 3-(3-ethylhexyl); 3-(1-propenyl); 3-(2-propenyl) and 3-(1,1,3,3-tetramethylbutyl), which are not claimed by this invention; 3-acetyl; 3-acetyl-5,5-dimethyl; 3-acetyl-4,4-dimethyl-5-propyl; 3-acetyl-5,5-diphenyl; 3-acetyl-4-ethyl-4-methyl; 3-acryloyl; 3-acetyl-4-ethyl;3-acetyl-4-methyl-5-phenyl; 3-acetyl-5-methyl-4-phenyl; 3-acetyl-4-phenyl; 3-acetyl-5-benzyl; 3-[2-(acetyloxy) ethyl]; 3-(acetyloxy)-4-(1-methylethenyl);-5-[(acetyloxy) methyl]-4-(hydroxymethyl); 5-[(acetyloxy)methyl]-3-(1-methylethyl);5-[(acetyloxy)-methyl]4-propyl; 3-[3-(acetyloxy) propyl]; 3-benzyl; 4-benzyl5, 5-diphenyl; 4,4-bis(hydroxymethyl); 3-benzyl-5-methyl;-3-benzyl-5-phenyl; 4-benzyl-4-phenyl; 3-butyl-5-methyl; 4-benzyl-4-methyl; 4-benzyloxy; 3-benzyl-4-phenyl; 5-butyl; 4-tert-butyl-5,5-dimethyl; 5-tertbutyl-5-methyl; 3-butyl-4-phenyl; 3-butyl-5-phenyl; 5-tert-butyl-4-phenyl; 3-butyl-5-[(2-propynyloxy)-methyl]; 5-(butoxymethyl)-3-butyl; 3-butyl-4,5,5-trimethyl; 3-butyl-5-(hydroxymethyl); 3-butyl-4-ethyl; 3-butyl-5-ethyl; 5-(3-cyclohexen-1-yl); 5-(3-cyclohexen-1-yl)-3-methyl; 3-cyclohexyl-5-methyl; 3-cyclohexyl-5-phenyl;- 5-cyclohexyl-3,4-diethyl; 5-cyclohexyl-4-ethyl; 5-cyclopentyl-4-ethyl; 5-cyclopropyl-5-methyl; 5-cyclopropyl-5-phenyl; 4,4-dimethyl; 3,4-dimethyl-5-phenyl;-5,5-diethyl; 5,5-diethyl-3-methyl; 5,5-dimethyl; 3,5-dimethyl-4-phenyl; 4,5-dimethyl-5-phenyl; 5,5-dimethyl-3-pivaloyl; 4,4-dimethyl-5-propyl; 4,4-diphenyl; 4,5-diphenyl; 5,5-diphenyl; 4,4-diethyl; 3-dodecyl-5-methyl; 4-decyl; 5-decyl; 5-decyl-3-dodecyl; 5-decyl-3-(2-hydroxydodecyl); 3,5-didodecyl; 4,5-diethyl; 4,5-dimethyl; 4,5-dioctyl; 4-dodecyl, 5-dodecyl; 5-dodecyl-3-(2-hydroxytetradecyl); 3-dodecyl-5-octyl; 3-dodecyl-5-tetradecyl; 5-decyl-3-ethenyl; 5,5-dicyclopropyl; 4-(1,1-dimethylethyl);3-(1,1-dimethylethyl)-5-(hydroxymethyl); 5-dodecyl-3-ethenyl; 5-dodecyl-3-methyl; 3-(1,1-dimethylethyl)-5-octyl;5,5-dimethyl-3-(1-methylethyl); 3,5-dimethyl-5-phenyl; 5,5-dimethyl-4-phenyl; 4,4-dimethyl-3-(2-propenyl); 3,4-dimethyl; 3,5-dimethyl; 3-(3,3-dimethyl-1-oxo-4-pentenyl); 4-ethyl;3-ethyl-5-methyl; 5-ethyl-4-methyl; 5-ethyl-3-methyl-5-phenyl; 5-ethyl; 4-ethyl-3-isopropenyl; 3-ethyl-5-methyl; 3-ethyl-4-methyl-5-phenyl; 4-ethyl-4-phenyl; 4-ethyl-3-vinyl;5-ethyl-3-vinyl; 3-(2-ethylbutyl)-4-(hydroxymethyl)-4-methyl; 4-ethyl-4-methyl; 3-(2-ethoxyethyl); 3-ethyl-4-methyl; 3-ethyl-5,5-dimethyl;-4-(1-ethyl-1-hydroxypropyl); 4-(1-ethyl-1-hydroxypropyl)-5-methyl;5-ethyl-5-methyl;3-(2-ethyl-1-oxo-4-pentenyl)-4-(1-methylethyl); 3-(2-hydroxyethyl); 4-(hydroxymethyl)-4-methyl; 4-(hydroxymethyl); 3-(2-hydroxypropyl)-5-methyl;3-hexyl-4-(hydroxymethyl)-4-methyl; 3-(2-hydroxyethyl)-5-methyl and its acetate, propionate, hexanoate, heptanoate, octanoate, pelargonate, decanoate, laurate, palmitate, stearate and oleate derivatives; 4-(hydroxymethyl)-3-isobutyl-4-methyl; 4-(hydroxy methyl)-4-methyl-3-neopentyl; 3-(3-hydroxypropyl)-5-methyl; 5-heptyl; 4-hexadecyl; 3-(4-hydroxybutyl); 3-(2-hydroxybutyl)-5-methyl; 3-(2-hydroxydecyl)- 5-octyl;3-(2-hydroxyhexadecyl)-5-tetradecyl;5-hexyl; 5-(hydroxymethyl);4-(1-hydroxy-2-methylpropyl); 3-(3-hydroxy-2,4-dimethyl-1-oxopentyl)4-(1-methylethyl);3-(3-hydroxy-2,4-dimethyl-1-oxopentyl)4-methyl-5-phenyl; 5-(hydroxymethyl)-3-(1-methylethyl); 4-(1-hydroxy-1-methylpentyl)-5-phenyl; 4-(hydroxymethyl)-5-phenyl; 4-(hydroxymethyl)-4,5,5-trimethyl; 3-(3-hydroxy-1-oxobutyl)-4-(1-methylethyl); 4-(1-hydroxyhexadecyl); 4-(1-hydroxyhexadecyl)-3-phenylmethyl; 4-(1-hydroxy-2-hexadecenyl); 4-(1-hydroxy-2-hexadecenyl)-3-phenylmethyl; 4-(hydroxymethyl)-5-methyl; 4-(1-hydroxy-1-phenylpropyl); 4-(1-hydroxy-1-phenylpropyl)-3-methyl;4-(1-hydroxy-1-phenylpropyl)5-methyl; 4-[1-hydroxy-1-(2-propenyl)-3-butenyl]; 4-[1-hydroxy-1-(2-propenyl)-3-butenyl]-5,5-diphenyl; 4-[1-hydroxy-1-(2-propenyl)-3-butenyl]-5-methyl; 4-[1-hydroxy-1-(2-propenyl)-3-butenyl]-5-phenyl; 3-(1-hydroxy-1-propenyl)-4-(1-methylethyl);4-(1-hydroxy-1-propylbutyl); 4-(1-hydroxy-1-propylbutyl)-5-phenyl; 3-(2-hydroxypropyl)-5-methyl; 4-(1-hydroxy-3-butenyl)-4,5-dimethyl-3-benzyl; 5-isobutyl-5-methyl; 3-isopenty5,5-dimethyl; 3-isovaleryl-5,5-dimethyl; 4-isobutyl; 5-isopropyl; 4-isopropyl-4-phenyl; 5-isobutyl-4,5-dimethyl; 3-(1-isobutoxyethyl); 4-isopropyl; 5-isopropyl4-phenyl; 4-methyl-5-phenyl; 4-methyl-5-propyl; 5-methyl; 4-methyl-4-phenyl; 5-methyl-5-phenyl; 4-methyl; 4-methyl-3-vinyl; 5-methyl-3-vinyl; 3-methyl-4,5-diphenyl; 5-methyl-4,5-diphenyl; 3-methyl-5,5-diphenyl; 4-methyl-4,5-diphenyl; 4-(1-methylethyl); 4-(1-methylethyl)-3-(1-oxobutyl); 4-(1-methylethyl)-3-(1-oxopropyl); 3-(1-methylethyl)-5-phenyl; 4-methyl-3-(2-methyl-1-oxobutyl)-5-phenyl; 4-methyl-3-(1-oxo propyl)-5-phenyl; 3-methyl-5-phenyl; 3-methyl-5-(phenylmethyl); 3-(2-methoxyethyl); 4-(1-methylethyl)3-(3-methyl-1-oxo-2-butenyl); 4-(1-methylethyl)-3-(2-methyl-1-oxobutyl); 4-(1-methylethyl)-3-(3-methyl-1-oxobutyl; oxobutyl; 4-(1-methylethyl)-3-(2-methyl-1-oxodecyl); 4-(1-methylethyl)-3-(2-methyl-1-oxo-4-pentenyl);4-(1-methylethyl)-3-(1-oxobutyl); 4-(1-methylethyl)-3-(1-oxodecyl); 4-(1-methylethyl)-3-(1-oxopropyl); 5-methyl-4-(3-methylbutyl); 5-methyl-4-(2-oxopropyl); 4-(1-methylethyl)-3-(2-methyl-1-oxohexyl); 4-methyl-3-(3-methyl-1-oxobutyl)-5-phenyl; 4-methyl-3-(4-methyl-1-oxo-3-pentenyl)-5-phenyl; 4-methyl-3-(2-methyl-1-oxopentyl)-5-phenyl; 4-methyl-3-(1-oxobutyl)-5-phenyl;-4-methyl-3-(1-oxopentyl)-5-phenyl; 4-methyl-3-(1-oxo propyl)-5-phenyl; 5-octyl; 3-(1-oxobutyl); 3-(1-oxodecyl);3-(1-oxoheptyl); 3-(1-oxohexyl); 3-(1-oxononyl); 3-(1-oxooctyl); 3-(1-oxopentyl); 3-(1-oxopropyl);3-(1-oxo-2-propenyl);3-(1-oxo-2-butenyl)-4-phenylmethyl; 3-(1-oxo-4-hexenyl)-4-(phenylmethyl); 3-(1-oxo-4-pentenyl)-4-(phenylmethyl); 3-(1-oxopropyl)-4-(phenylmethyl); 4-phenyl; 5-phenyl; 4-phenyl-3-vinyl; 5-propyl; 4-propyl; 3-propyl-5-[(2-propynyloxy)methyl]; 5-pentyl;4-phenylmethyl; 5-phenylmethyl; 5-(2-phenylethyl); 4,5,5-triphenyl; 4,5,5-trimethyl; 4-tetradecyl; 5-tetradecyl; 4,5,5-triethyl; 3,4,4-trimethyl; 4,4,5,5-tetramethyl,5-tridecyl; 3,5,5-trimethyl-4-phenyl and 3,5,5-trimethyl.

Volume 27, Part 4 of Beilsteins Handbuch der Organischen Chemie refers to the synthesis of 3-Acetyl, 4-Methyl, 6-Methyl, 3,5,5-Trimethyl and 5-Ethyl-5-phenyltetrahydro-1,3-oxazin-2-ones. In addition to these, Meyers and Adickes, Tet. Lett. 5151 (1969), reported preparation of 4,4,6-Trimethyl and 3,4,4,6-Tetramethyltetrahydro-1,3-oxazin-2-ones; Alewood et al., Can. J. Chem. 52, 4083 (1974), have synthesized 5,5-Dimethyl and4-Methyltetrahydro-1,3-oxazin-2-ones; Breslow et al., J. Amer. Chem. Soc. 89, 2384 (1967) obtained 4-Hexadecyloxazolidin-2-one in 5% yield and 4-Pentadecyltetrahydro-1,3-oxazin-2-one in 8% yield as minor products during thermolysis of n-Octadecyl azidoformate; Breslow and Ward, J. Org. Chem. 38, 4205 (1973), prepared 6-Methyltetrahydro-1,3-oxazin-2-one.

The following imidazolidin-2-ones and tetrahydropyrimidin-2-ones, encompassed by general formula I of this invention are known. Chemical Abstracts, Collective Volumes 1 through 11, and Volumes 106–107 -(up to 1987) disclose the following imidazolidin-2-ones: 1,3-dibutyl, 1,3-didodecyl, 1,3-diethyl, 1,3-diisopropyl, 1,3-dimethyl, 1,3-dioctyl, 1,3-dipropyl, 1-dodecyl, 1-dodecyl-3-methyl, 1-ethyl, 1-butyl-3-dodecyl, 1-butyl-3-octadecyl, 1,3-diallyl, 1,3-didecyl, 1-methyl-3-octadecyl, 1-octadecyl, 1-pentyl, 1-heptyl, 1-hexyl, 1-nonyl and 1-octyl, which are not claimed by this invention; 1-acetyl, 1-acetyl-5-hexyl, 1-acetyl-5-methyl, 1-acetyl-5-phenyl, 1-acetyl-3-propionyl, 4-benzyl-5-methyl, 4,5-bis(allyloxy), 1,3-bis[(allyloxy)methyl], 4,5-bis(2-butenyloxy), 4,5-bis(3-butenyloxy) 1,3-bis(butoxymethyl), 4,5-bis(dodecyloxy), 4,5-bis(hexenyloxy), 4,5-bis(hexyloxy), 1,3-bis(2-hydroxyethyl), 1,3-bis(hydroxymethyl), 1,3-bis(hydroxymethyl)4,5-dimethyl, 1,3-bis(hydroxymethyl)-4-methoxy4,5,5-trimethyl, 1,3-bis(hydroxymethyl)4,44-methyl,1,3-bis(hydroxymethyl)-4,4,5-trimethyl, 1,3-bis(hydroxymethyl)-4-octadecyl, 1,3-bis(1-isopropoxyethyl), 4,5-bis(2-methoxyethoxy)-1,3-dimethyl, 1,3-bis(1-methoxyethyl), 1,3-bis(methoxymethyl),1,3-bis(methoxymethyl)-4-methyl, 1,3-bis(methoxymethyl)-4-methyl-4,5-bis(octadecyloxy) 4,5-bis(octyloxy), 1,3-bis(1-oxobutyl), 1,3-bis(1-oxodecyl), 1,3-bis(1-oxoheptyl), 1,3-bis(1-oxohexyl), 1,3-bis(1-oxononyl), 1,3-bis(1-oxooctyl), 1,3-bis(1-oxopentyl), 1,3-bis(1-oxo-2-propenyl), 1,3-bis(1-oxopropyl),4,5-bis(3-pentenyloxy), 4,5-bis(4-pentenyloxy), 4,5-bis(pentyloxy), 4-(3-butenyl)-4-methyl, 1-(butoxymethyl)-3-methyl, 4-butyl, 1-butyl-4,4-diethyl-3-methyl-5-methylene, 4-butyl-4-ethyl, 1-butyl-3-ethyl-4,4-dimethyl-5-methylene, 4-butyl- 5-methyl, 1-butyl-3,4,4-trimethyl-5-methylene, 4-(1-cyclohexen-1-yl)-5-methyl, 1-cyclohexyl,1-cyclohexyl4-methyl, 4-cyclohexyl, 4-cyclohexylmethyl, 4-cyclohexyl-1-methyl, 4-cyclohexyl-4-methyl, 4-cyclohexyl-5-methyl, 4-cyclohexylmethyl-5-methyl, 1-cyclooctyl, 1-(4-cycloocten-1-yl), 4-cyclopentyl-4-methyl, 4-(decahydro-2-naphthyl), 1-decyl-3-(2-hydroxyethyl), 1,3-diacetyl, 1,3-diacetyl-4-benzyl1,3-diacetyl-4-benzyl-5-methyl, 4,5-dibutoxy, 4,5-dibutoxy-1,3-bis(hydroxymethyl), 1,3-dibutyl-4,5-dimethoxy, 1,3-dicyclohexyl, 1,3-diacetyl-4-methyl, 4,5-diethoxy, 4,5-diethoxy-1,3-bis(ethoxymethyl), 4,5-diethoxy-1,3-bis(hydroxymethyl), 4,5-diethoxy-1,3-dimethyl, 4,4-diethyl, 1,3-diethyl-4,5-dimethoxy, 1,3-diethyl-4,4-dimethyl-5-methylene, 4,5-diisobutoxy, 4,4-diisobutyl, 4,5-diisopropoxy, 4,5-diisopropoxy-1,3-dimethyl, 4,5-diisopropyl-1,3-dimethyl4,5-dimethoxy,4,5-dimethoxyl,3-bis(methoxymethyl), 4,5-dimethoxy-1,3-dimethyl, 4,5-dimethoxy-1-(methoxymethyl)-3-methyl, 4,5-dimethoxy-3-(methoxymethyl)-1-octadecyl,4,5-dimethoxylmethyl, 4,4-dimethyl, 4,5-dimethyl, cis- and trans-4,5-dimethyl-1-phenylmethyl, 1,3-dimethyl-4,4-diphenyl, 1,4-dimethyl-4-phenyl, 1,5-dimethyl-4-phenyl, 1,4-dimethyl-4,5-dipropoxy, 1-(1,1-dimethylethyl)-5,5-dimethyl, 5,5-dimethyl-1-(2-phenylethyl), 4,4-diphenyl, 4,5-diphenyl4,5-dipropoxy, 4,4-dipropyl, 4,5-dipropyl, 4-dodecyl, 4-dodecyl-5-methyl, 1-ethyl5,5-dimethyl, 3-ethyl,1,4-dimethyl-5-methylene-4-phenyl, 4-ethyl-1,3-dioctyl, 4-ethyl-4-isopentyl, 1-ethyl-4-methyl, 4-ethyl-5-methyl, 4-(1-ethylpentyl), 4-ethyl-4-phenyl, 4-heptyl, 4-hexyl, 1-hexyl-3-(2-hydroxyethyl), 4-hexyl-5-methyl, 1-(2-hydroxyethyl), 1-(2-hydroxyethyl)-4-phenyl, 4-isobutyl-4-methyl, 1-isopropyl-4,4dimethyl, 4-methoxy-5,5-dimethyl-1-(1-methylethyl), 4-methoxy5,5-dimethyl-4-phenyl, 1-(1-methoxyethyl), 1-(2-methoxy ethyl), 1-(2-methoxyethyl)4-phenyl, 1-(methoxymethyl), 4-methoxy-4,5,5-trimethyl, 4-methyl, 4-methyl1,3-dioctyl, 1-methyl4,4-diphenyl, 1-methyl-4,5-diphenyl, 1-methyl-5,5-diphenyl, 4-(1-methyl ethyl), 4-methyl-4- nonyl, 4-methyl-4-pentyl, 1-methyl-4-phenyl, 4-methyl-4-phenyl, 4-methyl-5-phenyl, 4-octyl, 1-(1-oxobutyl), 1-(1-oxodecyl), 1-(1-oxononyl), 1-(1-oxooctyl), 1-(1-oxopropyl), 4-pentyl, 4-phenyl, 4-phenyl-4-propyl, 1-propionyl, 4-propyl, 4,4,5,5-tetramethyl, 1,3,4,4-tetramethyl-5-(2-methyl-1-propenyl), 1,3,4,4-tetramethyl-5-(1-propenyl), 1,3,4-trimethyl, 1,3,4-trimethyl-5-(2-methyl-1-propenyl) and 1,3,4-trimethyl5-(1-propenyl). Volume 24, Part 1 of Beilsteins Handbuch der Organischen Chemie discloses the synthesis of the following tetrahydropyrimidin-2-ones: 1,3-dimethyl, 1-isopropyl, 4-methyl, 5,5-dimethyl, 5-ethyl 5-methyl, 4,4,6-trimethyl, 5-methyl-5-propyl, 5,5-diethyl, 5-isobutyl-5-methyl, 5-methyl-5-pentyl, 5-ethyl-5-butyl, 5,5-dipropyl, 5-ethyl-5-(1-methylbutyl), 5-ethyl-5-isopentyl, 5,5-diisobutyl, 5-cyclohexylmethyl, 5-allyl-5-(1-methylbutyl), 5,5-diallyl, 5-cyclohexyl-4-cyclohexylmethyl, 4,6-dicyclohexyl-4-methyl, 5-phenyl, 4-benzyl, 5-benzyl, 5-methyl-5-phenyl, 5-ethyl-5-phenyl, 5-phenyl-5-propyl and 5-isopropyl-5-phenyl. In addition to these, Li et al., J. Med. Chem. 24, 1089 (1981), have reported 1,3-diethyl and 1,3-dibutyltetrahydro-pyrimidin-2-ones as inducers of Murine Erythroleukemia differentiation.

The following cyclic carbonates, encompassed by the general formula I of this invention, are known in the prior art. Chemical Abstracts, Collective Volume 1-11 and Volumes 106-107 (up to 1987) disclose the following 1,3-dioxolan-2-ones: 4-(allyloxy)methyl; 4-(1-butylvinyl); 4,5-dimethyl;4-hydroxymethyl, 4-methyl; 5-methyl; 4-vinyl; 4,4-dimethyl; 4,5-dimethyl-4,5-diphenyl; 4-ethyl; 4-phenyl; 4,4,5,5-tetramethyl;4,4,5-trimethyl; 4-hydroxybutyl; 4-(2-hydroxyethyl);4-cyclohexyl; 4,5-dipropyl; 4-methoxymethyl; 4-[(phenylmethoxy)methyl]; 4-(1,2-dihydroxybutyl); 4-ethyl-4,5,5-trimethyl; 5-methyl-4,4-diphenyl; 4-methyl-5-phenyl; 4-heptadecyl; 4-[(1,9-octadecadienyloxy)methyl]; 4-[1-methyl-2-(phenylmethoxy) ethyl]; 4-[1-hexadecenyloxy)methyl]; 4,5-diphenyl; 4-butyl; 4,4-dimethyl-5-(phenylmethyl); 4-heptyl-5-methyl; 4,4-dimethyl-5-(3,7,12,16-tetramethyl-3,7,11,15-octadecatetraenyl); 4-hexyl; 4-[(hexadecyloxy)methyl];4-[(acetoxy)methyl]-5-phenyl;4-(hydroxymethyl)-5-[(phenylmethoxy)methyl]; 4-(1-hydroxy-3-butenyl)-5-methyl; 4-(1-hydroxyethyl)-5-(2-propenyl); 4-[1-hydroxy-2-(phenylmethoxy)ethyl]; 4-[(1,1-dimethylethoxy)methyl]; 4-[(1-methylethoxy)-methyl]; 4-(butoxymethyl); 4-(1,1-dimethylethyl); 4-(5-hexenyl); 4-(1-hydroxy-4-methyl-4-hexenyl)-4-methyl; 4-(1-methylethyl); 4,5-bis(phenylmethyl); 5-(1-hydroxyethyl)-4-methyl-4-(2-propenyl); 4-(hydroxymethyl)-5-pentyl; 4-(cyclohexylmethyl); 4-(cyclohexylmethyl)-4-methyl and 4-(cyclohexylmethyl)-5-methyl.

The following 1,3-dioxan-2-ones are known in the prior art: 5,5-diethyl; 5,5-dimethyl; 5-methyl-5-propyl; 5-butyl-5-ethyl and 5-ethyl-5-phenyl [Ludwig and Piech, J. Amer. Chem. Soc. 73, 5799 (1951)]; 5-hydroxymethyl-5-methyl, 4-propyl-5-ethyl; 4,6-dimethyl; 4,4,6-trimethyl and 5-ethyl-5-phenyl [Searles et al., J. Org. Chem. 27, 2828 (1962) and references cited therein].

To my knowledge the other compounds are novel.

The use of the compounds of the present invention as penetration enhancers is, however, novel and not predictable from the prior art. Moreover, majority of cyclic urethanes known in the prior art, with the exception of those mentioned by Foglia and Swern, J. Org. Chem.32, 75 (1967); Dyen and Swern, J. Org. Chem. 33, 379 (1968) and J. Amer. Oil Chem. Soc. 45, 325 (1968); Herweh et al., J. Org. Chem. 33, 4029 (1968); Bal'on and Moskaleva, J. Org. Chem. U.S.S.R. 11, 2565 (1975); Culbertson and Dietz, J. Polymer Sci., Part A1, 9, 2727 (1971); Naumov et al., C.A. 85: 123067 q-(1976); Julina et al., Helv. Chim. Acta 69, 368 (1986); Patrick et al., J. Org. Chem. 43, 2628 (1978); Hickner, U.S. Pat. No. 3,190,885 (June 22, 1965); Bernet and Vasella, Tetrahedron Lett. 24, 5491 (1983), have alkyl-group or groups on the ring carbons with less than four carbon atoms. These compounds are soluble in water and are therefore not expected to have comparable penetration enhancing properties to that of the compounds claimed by this invention. The N-higher alkyl substituted cyclic urethanes, described on p. 2519, Vol. 27, Part 4 of Beilsteins Handbuch der Organischen Chemie and in Chemical Abstracts Collective Vol 1-11 and Vol. 106 (up to 1987), are not claimed by this invention. Naumov et al., C.A. 85: 123067 q-(1976), describe that the 3-(1-oxoalkyl)oxazolidin-2-ones are inactive as insect repellents.

Higuchi and Pogany, U.S. Pat. No. 4,667,131 -(June 30, 1987) have described the use of novel imidazolidin-2-ones substituted in 1 and 3 positions with aryl, aralkyl and alkyl groups as dermal penetration enhancers and, in particular, 1-methyl-3-heptyl, 1-methyl-3-decyl and 1-methyl-3-dodecylimidazolidin-2-ones, when formulated with beta-lactam antibiotics, antiviral agents, neoplasm inhibitors, amino acids, muscle relaxants, inflammation inhibitors and diuretics. However, two of the three specific compounds mentioned in their disclosure as novel are known in the prior art, C.A. 63: P 11572d (1965). Also, any data to substantiate the claimed use of these compounds as dermal penetration enhancers has not been disclosed in detailed description of their invention. Ito et al., C.A. 105: 49055x (1986), disclose topical pharmaceutical bases, containing cyclic ureas with hydrogen and lower alkyl substituents on nitrogen atoms, for accelerating drug absorption through the skin. Satoh et al., U.S. Pat. No. 4,594,243, disclose compositions containing 1,3-di-loweralkyl substituted cyclic ureas as percutaneous absorption enhancers for Diazepam and Clonidine and claim specifically 1,3-dimethylimidazoli din-2-one. However, a composition containing 97% of 1,3-dimethylimi dazolidin-2-one with 3% Diazepam shows poor blood levels when compared to compositions containing 97% DMSO or 72% 1,3-dimethylimidazolidin-2-one with 25% of an additional adjuvant. With Clonidine no significant differences in tail arterial blood pressure in rats were seen when composition containing 0.8% drug in 75.2% 1,3-dimethylimidazolidin-2-one and 25% isopropyl myristate was compared to the one with 99.2% 1,3-dimethylimidazolidin-2-one and to the one with 99.2% DMSO. All compositions disclosed by Satoh et al. contain from 75 to 99% of 1,3-dimethylimidazolidin-2-one, an unusually high proportion for an absorption enhancer in a composition. The compound seems to fulfill the criteria of a solvent rather than an exepient, which is generally used up to 10% in a composition. Similarly, Abe et al., C.A. 105: 158834w (1986), disclose topical formulation of 1% Diazepam in 74% ethanol and 25% 1,3-dipentylimidazolidin-2-one and claim that the cyclic urea, when combined with a polar substance such as ethanol, potentiates the drug transport. This composition, similar to those of Satoh et al. above, utilizes very high amount (74%) of ethanol, a known skin permeation enhancer, and considerably high amount (25%) of a cyclic urea disclosed as an enhancer. It is highly likely that the high percentage of ethanol would mask the effect of the cyclic urea as an enhancer. Moreover, 1,3-dimethylimidazolidin-2-one utilized by Satoh et al. is water soluble and therefore is expected to behave differently when compared to the imidazolidin-2-ones disclosed by Higuchi and Pogany and by Abe et al. mentioned above. Moreover, all these N1 and N3 alkyl substituted imidazolidin-2-ones are not claimed by my invention. Also, it would not be predictable from this prior art and would not be obvious to the one skilled in the art that imidazolidin-2-ones and related cyclic ureas substituted with aryl, aralkyl, alkyl, cycloalkyl, hydroxyalkyl, acyloxyalkyl, alkoxyalkyl and alkoxy groups specifically on the ring carbons and additionally on nitrogens would show skin penetration enhancing properties. 4,5-dialkoxyimidazolidin-2-ones have been disclosed [Takaya et al., C.A. 60: 5512 a (1964) and Seki and Segawa, Chem. Pharm. Bull. 12, 843 (1964)] as sedatives, hypnotics and antispasmodics. 1,3-dialkyl-4,5-dialkoxyimidazolidin-2-ones have been disclosed [Burris, Belg. 614,590 (Sept. 3, 1962); Beachem and Van Loo, Belg. 614,586 (Sept. 3, 1962)] as cellulose textile finishing agents.

The prior art discloses only the use of propylene carbonate, (4-methyl-1,3-dioxolan-2-one), alone and in two cases in combination with ethylene carbonate (1,3-dioxolan-2-one), in pharmaceutical and herbicidal compositions. Shastri and Shaik, Ger. Offen. 2,153,779 (08 Jun 1972); Inoe et al., Jap. Kokai Tokkyo Koho 80 24,131 (21 Feb 1980); C.A. 93: 173726 q (1980) used propylene carbonate in an ointment base compositions for topical application of antiinflammatory steroids; it was used as a solubilizing agent for topical steroid, Fluclorone acetonide, Malone et al., Brit. J. Dermatol. 90, 187 (1974) and for Nifedipine, Matsuno et al., Jpn. Kokai Tokkyo Koho 79 55,174 (04 May 1979); C.A. 91: 160375 s (1979); Kudla, Belg. 886,913 (30 June 1981); C.A. 95: 121168 f (1981) used ethylene carbonate and Nippon Redarii K.K., Jpn. Kokai Tokkyo Koho JP 82 98,208 (18 June 1982); C.A. 97: 188270 t (1982) disclosed a combination of ethylene and propylene carbonates as a solubilizing agent for amcinonide in ointment formulations. The latter claimed that this ointment improve drug transport through the skin. However, Ishihara, C.A. 105: 48896 k (1986) showed that addition of ethylene carbonate to the composition did not improve the efficacy. Propylene carbonate was used as a solubilizing agent in antiinflammatory and analgesic gel compositions containing ketoprofen and flurbiprofen, Noda et al., U.S. Pat. No. 4,393,076 (12 July 1983); in a solid antiperspirant stick composition, Nabial, U.S. Pat. No. 4,425,328 (10 Jan. 1984), in stable ointment bases for indomethacin and bufexamac, Nippon Lederle Co., Ltd. Jpn. Kokai Tokkyo Koho JP 59 70,612 (21 Apr. 1984); C.A. 101: 78850 a (1984); in cream formulations for ketoprofen, Hokuriku Pharmaceuticals Co. Ltd. Jpn Kokai Tokkyo Koho JP 59 190,912 (29 Oct. 1984); C.A. 102: 50926 b (1985). It has also been used as a dispersant for water in oil emulsions in aerosol compositions, Hughett, Ger. Offen. 2,850,488 (23 May 1979); C.A. 91: 198786 f (1979); Showa Denko K.K., Jpn. Kokai Tokkyo Koho 80 69,681 (26 May 1980); C.A. 93: 181030 y (1980); Toyo Aerosol Industry Co. Ltd., Jpn. Kokai Tokkyo Koho 80,142, 073 (6 Nov. 1980); C.A. 94: 52706 v (1981) and as an antimicrobial agent (preservative), Kobayashi Kose Co. Ltd., Jpn. Kokai Tokkyo Koho 80,167,210 (26 Dec. 1980); as a skin cleaner for removing paints, Elepano et al., U.S. Pat. No. 4,508,634 (2 Apr. 1985) and in hair dyeing composition, Herlihy, Eur. Pat. Appl. EP No. 161,073 (13 Nov. 1985); C.A. 104: 155705 y (1986); in makeups containing oils, metallic filaments and montmorillonite clay for ear lobes, Shimoyama et. al., Jpn. Kokai Tokkyo Koho JP 60,214,723 (28 Oct 1985); C.A. 104: 115888 d (1986); as a solvent in herbicidal mixture, Roth, Eur. Pat. Appl. EP No. 189,588 (06 Aug 1986); C A. 106: 1840 t (1987) and in a gel composition for protection against urushiol, Powell et al., Eur. Pat. Appl. EP No. 219,054 (22 Apr. 1987); C.A. 107: 46279 d (1987). Both ethylene and propylene carbonates are water soluble and are not expected to enhance permeation of drugs into and through the skin as do the cyclic carbonate enhancers of this invention, which contain at least 5 or more carbon atoms on the cyclic carbonate ring structure. Barry et al., J. Pharm. Pharmacol. 37, 226 (1985) have looked at vapor and liquid permeation through human skin of several model penetrants and concluded that propylene carbonate produced low flux and thus is a poor permeation enhancer. The cyclic carbonates of this invention are primarily lipophilic in nature as compared to ethylene and propylene carbonates, which are hydrophilic and therefore are mainly used as solubilizing agents in compositions of the prior art. At very high concentrations these compounds, similar to solvents such as DMSO, DMF, 2-pyrrolidone and N-methyl-2-pyrrolidone, may show permeation of drugs and other materials through the skin altering most likely the skin barrier considerably. In contrast, the cyclic carbonates of this invention have been efficacious below 10% concentration as permeation enhancers. The cyclic urethanes, covered by the general formula I of this invention, may be prepared by any of the processes known in the prior art. These have been reviewed by Dyen and Swern, Chem. Rev. 67, 197 (1967). Also known in the prior art are synthetic methods described by Foglia and Swern, J. Org. Chem. 32, 75 (1967); Dyen and Swern, J. Org. Chem. 33, 379 (1968); Jones and Witty, J. Chem. Soc. Perkin I, 858 (1980); Kondo et al., Angew. Chem. Int. Ed. Engl. 18, 692 (1979); Sonoda et al., Tet. Lett. 1969 (1975), Rajca et al., Synthesis 1032 (1983), Eckstein and Urbanski, Adv. Hetero. Chem., Vol. 23 (1978), Kim and Ko, Heterocycles 24, 1625 (1986); Baba et al., Tetrahedron Lett. 27, 77 (1986); Lorincz and Erden, Synth. Commun. 16, 123 (1986); Julina et al., Helv. Chim. Acta 69, 368 (1986); Tam, J. Org. Chem. 51, 2977 (1986); Roush and Adam, J. Org. Chem. 50, 3752 (1985); Miyahara et al., Chem. Pharm. Bull. 33, 497 (1985); Hamaguchi et al., Eur. Pat. Appl. EP No. 123,719 (7 Nov. 1984); Bernet and Vasella, Tetrahedron Lett. 24, 5491 (1983); Bal'n and Moskaleva, J. Org. Chem. U.S.S.R. 11, 2565 (1975); Hassner and Burke, Tetrahedron, 30, 2613 (1974); Wada and Oda, Bull. Chem. Soc. Japan 43, 2167 (1970); Li and Biel, J. Org. Chem. 35, 4100 (1970); Bestian et al., Ger. Pat. 1,273,533 (25 July 1968) ; C.A. 69, 96457 c (1968); Jefferson Chemical Co., Inc., Brit. Pat. No. 883,994 (6 Dec. 1961);C.A. 58: 2454 g (1963); Bruno et al., J. Org. Chem. 26, 2253 (1961); Speranza and Peppel, J. Org. Chem. 23, 1922 (1958); Gulbins et al., Chem. Ber. 93, 1975 (1960); Pirkle and Simmons, J. Org. Chem. 48, 2520 (1983); Sullivan and Efner, J. Org. Chem. 33, 2134 (1968); Hassner et al., J. Org. Chem. 32, 540 (1967) and Boucherle et al., Bull. Soc. Chim. France 231 (1957). All these synthetic methods are hereby incorporated herein by this reference.

The 3-alkyl and alkoxyalkyl substituted cyclic urethanes of this invention may be prepared by treatment of an appropriate cyclic urethane with an alkyl halide, alkyl sulfate or related alkylating agents in presence of a base, for example sodium hydride, in a polar aprotic solvent, for example anhydrous dimethyl formamide, as described by Meyers and Adickes, Tet. Lett. 5151 (1969); Jaiswal and Parmar, J. Hetero. Chem. 15, 519 (1978), Close, J. Amer. Chem. Soc. 73, 95 (1951), Nguyen et al., C.A. 106: 196309 g (1987); Nisso Petrochemical Industries, C.A. 98: 53866 s (1983).

The 3-acylated cyclic urethanes of this invention may be prepared by acylation of a cyclic urethane with a carboxylic acid anhydride or acid chloride as described by Homeyer, U.S. Pat. No. 2,399,118 (23 Aug. 1946) and by Close, J. Amer. Chem. Soc. 73, 95 (1951), Naumov et al., C.A. 85: 123067 q (1976) and Hickner, U.S. Pat. No. 3,190,885 (22 June 1965).

The cyclic ureas, covered by the general formula I of this invention, may be prepared by any of the processes known in the prior art. For example, these methods have been described by J. W. Cornforth, Vol. 5, Heterocyclic Compounds, Ed. Elderfield, pp. 250-251; Jung and Kohn, J. Amer. Chem. Soc. 107, 2931 (1985) and references cited therein; Bartmann et al., Tet. Lett. 25, 733 (1984) and references cited therein; Ghomi and Orr, Chem. Ind. 928 (1983); Quast and Nahr, Chem. Ber. 117, 2761 (1984); Aelony and McKillip, U.S. Pat. No. 3,876,657 (8 Apr. 1975); C.A. 83: 58825 c (1975); J. Hetero. Chem. 9, 687 (1972); Hata and Watanabe, Tetrahedron 30, 3569 (1974); Gulbins et al., Liebigs Ann. Chem. 698, 180 (1966); Scherer and Schmidt, Chem. Ber. 98, 2243 (1965); Cortes et al., J. Med. Chem. 28, 601 (1985); Beck et al., Ger. Offen. DE 3,337,180 (25 Apr. 1985); C.A. 103: 196078 u (1985); Orr and Miah, Chem. Ind. 392 (1983); Naumov et al., C.A. 78: 97557 h (1973); Arnold et al., Tetrahedron Lett. 137 (1969); Caron et al., Fr. M 5677 (12 Feb. 1968); C.A. 71: 38963 v (1969); Beachem, U.S. Pat. No. 3,304,312 (14 Feb. 1967); C.A. 66: 85789 z (1967); Astra-Werke A.G., Belg. 671,528 (Feb. 1966); C.A. 65: 15387 f (1966); Granger et al., C.A. 64, 14104 b (1966); Fusco et al., J. Org. Chem. 31, 313 (1966); Petersen et al., German Patent No. 1,172,265 (18 June 1964); C.A. 61: 9504 g (1964); Takaya et al., Japan 26383 (16 Dec. 1963); C.A. 60: 5512 a (1964); Burris, Belg. 614,590 (3 Sept. 1962); C.A. 58: 10207 b (1963); Stoffel and Speziale, J. Org. Chem. 28, 2917 81963) and references cited therein; Yost, U.S. Pat. No. 2,880,208 (31 Mar. 1959); C.A. 54: 569 (1960); Wilson, U.S. Pat. No. 2,517,750 (8 Aug. 1950); C.A. 45: 1627 i (1951); Duschinsky and Dolan, J. Amer. Chem. Soc. 67, 2079 (1945) and references cited therein; Rajca et al., Synthesis, 1032 (1983); Li et al., J. Med. Chem. 24, 1089 (1981); Kondo et al., J. Org. Chem., 44, 4430 (1979) and references cited therein; Skinner et al., J. Pharm. Sci. 68,391 (1979); Schoellkopf et al., Ann. 600 (1980); Richter et al., U.S. Pat. No. 4,154,931 (15 May 1979) and references cited therein; De Kimpe et al., Bull. Soc. Chim. Belge, 86, 663 (1977); Petersen, Ann. 726, 89 (1969) and references cited therein; Vail et al., J. Org. Chem. 30, 2179 (1965); Smirnov and Spasskaya, Zh. Obsch. Khim. 35, 180 (1965); Beachem and Van Loo Jr., Belg. 614,586 (3 Sept. 1962) C.A. 58: 10348c (1963); Palazzo and Cecinati, C.A. 51: 5086i (1957); Skinner et al., J. Amer. Chem. Soc. 79, 3786 (1957); Marshall, J. Amer. Chem. Soc. 78, 3696 (1956); Martell and Frost, J. Amer. Chem. Soc. 72, 1032 (1950); and K. Hoffmann in "Imidazole and its derivatives," Interscience Publishing Co., New York, 1953, pp. 213-245. All these synthetic methods are hereby incorporated herein by this reference.

The aminoalcohols used as starting materials for the preparation of some cyclic urethanes may be prepared according to the method of Evans et al., J. Org. Chem. 39,914 (1974) and references cited therein; Seki et al., Chem. Pharm. Bull. 13, 995 (1965) and references cited therein; Venkateswaran and Bardos, J. Org. Chem. 32, 1256 (1967); Swift and Swern, J. Org. Chem. 32, 511 (1967) and Patrick et al., J. Org. Chem. 43, 2628 (1978) and references cited therein. The diamines, necessary as starting materials for the preparation of cyclic ureas, may be prepared according to Jung and Kohn, J. Amer. Chem. Soc. 107, 2931 (1985)and references cited therein; Nielson, J. Org. Chem. 27, 1998 (1962); Hiyama et al., Tetrahedron 29, 3137 (1973); O'Gee and Woodburn, J. Amer. Chem. Soc. 73, 1370 (1951); Linsker and Evans, J. Amer. Chem. Soc. 67, 1581 (1945); Becker et al., J. Amer. Chem. Soc. 102, 5676 (1980); Kempter and Moser, J. Prakt. Chem. 34, 104 (1966) and Stevens et al., J. Org. Chem. 29, 3146-(1964). Hawkins, U.S. Pat. No. 2,587,043 (Feb. 26, 1952); Hawkins and Diggs, J. Amer. Chem. Soc. 71, 2530 (1949).

The cyclic carbonates, covered by the general formula I of this invention, may be prepared by any of the processes known in the prior art. For example, treatment of an appropriately substituted 1,2 or 1,3-diol with a carbonylating agent such as diethyl carbonate, phosgene, alkyl chloroformate, carbonyldiimidazole or treatment of an oxirane with β-butyrolactone affords a cyclic carbonate. These methods have been described by Kim and Ko, Heterocycles 24, 1625 (1986); Nishikubo et al., Tetrahedron Lett. 27, 3741 (1986) and references cited therein; Lorincz and Erden, Synth. Commun. 16, 123 (1986); Tam, J. Org. Chem. 51, 2977 (1986); Murthy and Dhar, J. Hetero. Chem. 21, 1721 (1984); Synth. Commun. 14, 687 (1984) and Najer et al., Bull. Soc. Chim. France, 1142 (1954). Fujita et al., [C.A. 77: 139451 f (1972)], disclose synthesis of cyclic carbonates from reaction of an oxirane with carbon dioxide in the presence of halides of Cr, Mn, Ru, Rh or Cd; this reaction is also carried out using a different catalyst by Naito et al., C.A. 96: 181176 n (1982); Szakacs et al., C.A. 97: 182250. q (1982); Rokicki et al., Monatsh. Chem. 115, 205 (1984); Ninagawa et al., Chem. Express 1, 169 (1986) and by Brindoepke and Marten, C.A. 107: 156951 z and 237911 p (1987); Kao and Sheng, U.S. Pat. No. 4,231,937 (4 Nov. 1980), C.A. 94: 102853 p (1981) prepared cyclic carbonates from alkylene iodohydrins and carbon dioxide at elevated temperature and pressure under catalytic conditions; Renga and Periana-Pillai, U.S. Pat. No. 4,332,779 (1 Jun. 1982) cyclized a βhaloalkyl carbonate in presence of mercuric acetate to get a cyclic carbonate. These methods are hereby incorporated herein by this reference.

The compounds of the present invention may be used as penetration enhancers in the same manner as described in my U.S. Pat. Nos. 3,989,816; 3,991,203; 4,415,563; 4,122,170; 4,316,893; 4,423,040; 4,424,210 and 4,444,762, and pending U.S. application Ser. Nos. 783,621 filed Sept. 30, 1985 and 002,387 filed Jan. 12, 1987, which are hereby incorporated by reference.

The compounds of the present inventions are useful as penetration enhancers for a wide range of physiologically active agents and the compositions disclosed herein are useful for topical and transdermal therapeutic effect of these agents. Typically, systemically active agents which may be delivered transdermally are therapeutic agents which are sufficiently potent such that they can be delivered through the skin or other membranes to the bloodstream in sufficient quantities to produce the desired therapeutic effect. In general, this includes agents in all of the major therapeutic areas including, but not limited to, anti-infectives, such as antibiotics and antiviral agents, analgesics, anorexics, anthelmintics, antiarthritics, antiasthma agents, anticonvulsants, antidepressants, antidiabetic agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, sedatives and tranquilizers and anti-osteoporosis agents.

For topical applications the agents include antibiotics, fungistatic and fungicidal agents, corticosteroids, antihemorrhoidal agents, antiinflammatory agents, antineoplastic agents, antiemetics, antipruritic agents, vasodilators, bronchodilators, expectorants, analgesics, sunscreen compounds, collagen softening agents and other similar compounds. Cosmetic agents, hair and skin dyes, natural and synthetic hormones, perfumes, insect repellents, diagnostic agents and other such compounds may also be advantageously formulated with these penetration enhancers.

Moreover, these penetration enhancers are useful in agriculture in the application of fertilizers, hormones, growth factors including micronutrients, insecticides, molluscicides, arichicides, nematocides, rodenticides, herbicides, and other pesticides to plants, animals and pests. These penetration enhancers are also useful for penetration of micronutrients in seeds for enhanced plant growth.

Of course, the appropriate dosage levels of all the physiologically active agents, without conjoint use of the penetration enhancing compounds of formula I, are known to those of ordinary skill in the art. These conventional dosage levels correspond to the upper range of dosage levels for compositions including a physiologically active agent and a compound of formula I as a penetration enhancer. However, because the delivery of the active agent is enhanced by compounds of the present invention, dosage levels significantly lower than conventional dosage levels may be used with success. Systemically active agents are used in amounts calculated to achieve and maintain therapeutic blood levels in a human or animal over the period of time desired. (The term "animal" as used here encompasses humans as well as other animals, including particularly pets and other domestic animals.) These amounts vary with the potency of each systemically active substance, the amount required for the desired therapeutic or other effect, the rate of elimination or breakdown of the substance by the body once it has entered the bloodstream and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The present invention contemplates compositions of compounds of formula I, together with physiologically active agents from 0.05% to 100% of conventional dosage levels. The amount of cyclic urethane or cyclic urea derivative which may be used in the present invention is an effective, non-toxic amount for enhancing percutaneous absorption. Generally, for topical use the amount ranges between 0.01 to about 10 and preferably about 0.1 to 5 percent by weight of the composition. For transdermal enhancement of systemic agents, the amount of penetration enhancer which may be used in the invention varies from about 1 to 100 percent, although adequate enhancement of penetration is generally found to occur in the range of about 1 to about 30 percent by weight of the formulation to be delivered. For transdermal use, the penetration enhancers disclosed herein may be used in combination with the active agent or may be used separately as a pre-treatment of the skin or other body membranes through which the active agent is intended to be delivered.

Dosage forms for application to the skin or other membranes of humans and animals include creams, lotions, gels, ointments, suppositories, sprays, aerosols, buccal and sublingual tablets and any one of a variety of transdermal devices for use in the continuous administration of systemically active drugs by absorption through the skin, oral mucosa or other membranes, see for example, one or more of U.S. Pat. Nos. 3,598,122; 3,598,123; 3,731,683; 3,742,951; 3,814,097; 3,921,636; 3,972,995; 3,993,072; 3,993,073; 3,996,934; 4,031,894; 4,060,084; 4,069,307; 4,201,211; 4,230,105; 4,292,299 and 4,292,303. U.S. Pat. No. 4,077,407 and the foregoing patents also disclose a variety of specific systemically active agents which may also be useful as in transdermal delivery, which disclosures are hereby incorporated herein by this reference.

Typical inert carriers which may be included in the foregoing dosage forms include conventional formulating materials, such as, for example, water, ethanol, 2-propanol, 1,2-propanediol,1,3-butanediol, 1,2,3-propanetriol, propanone, butanone, carboxylic acid esters such as isopropyl myristate, diisopropyl adipate and diisopropyl sebacate, acyclic and cyclic amides including N-methyl pyrrolidone, 1-dodecylhexahydro-2H-azepine-2-one and 1-dodecanoyl-hexahydro 1H-azepine, freons, polyvinyl pyrrolidone, fragrances, gel producing materials such as "Carbopol," stearyl alcohol, stearic acid, spermaceti, sorbitan monooleate, sorbital, "Polysorbates", "Tweens", methyl cellulose, etc.

It will be readily appreciated by those skilled in the art that certain compounds represented by general formula I exhibit chirality. However, where no designation of isomers is specified with respect to the compounds of this invention, it is to be understood that all possible stereoisomers are included.

The examples which follow illustrate the penetration enhancers and the compositions of the present invention. However, it is understood that the examples are intended only as illustrative and are not to be construed as in any way limiting to the scope of this invention.

EXAMPLE 1

Preparation of 4-Decyloxazolidin-2-one 26.465 g of 2-aminododecanol and 12.32 g of ethylene carbonate were heated at approximately 110° C. for 48 hours (preparation of the cyclic urethanes can be carried out without a solvent or in toluene solution) as a solvent. The reaction was followed by tlc and at the completion of the reaction the contents were cooled, dissolved in ethyl acetate and the organic solution was washed with brine and water. After drying, the filtrate was concentrated and the oily residue was kugelrohr distilled to give 27.33 g (96.56%) of colorless liquid, which slowly solidified, m.p. 31.5–32.5° C.

EXAMPLE 2

Preparation of 3-methyl-4-decyloxazolidin-2-one

A solution of 2.5 g of compound obtained under Example 1 in 20 ml of dry DMF was added to a cooled, stirred suspension of 0.5 g of hexane-washed sodium hydride (60% NaH dispersion in oil) in 50 ml of dry DMF. The mixture was stirred for 1 hour at ambient room temperature (r.t.), heated at ~100 C until hydrogen evolution had ceased (approximately 1 hour). After cooling, 2 ml of iodomethane was added and the reaction mixture was allowed to stir at r.t. for 48 hours. The contents were poured into cold dilute HCl solution and extracted with 3×25 ml of ether. The combined organic extracts were washed with brine, dried and concentrated to an oil. Kugelrohr distillation at 130°–140° C./ 0.3 mm Hg gave 2.6 g (98%) of product.

EXAMPLE 3

Preparation of 3-acetyl-4-decyloxazolidin-2-one 2.3 g of compound obtained under Example 1 was mixed with 10 ml of triethylamine and 50 ml of chloroform and was reacted with 3 g of acetic anhydride. The reaction mixture was allowed to stir overnight at r.t., then refluxed for 2 hours, cooled and poured into cold saturated bicarbonate solution. After the excess acetic anhydride was destroyed the aqueous layer was extracted with 3×20 ml of ether. The combined organic extracts were dried and concentrated to give an oil, which solidified on standing. Recrystallization from ether/hexane afforded 1.73 g (64%) of white crystals, m.p. 51°–53° C.

EXAMPLE 4

Preparation of (R)-4-benzyloxazolidin-2-one 3 g of (R)-(+)-2-amino-3-phenylpropanol and 1.8 g of ethylene carbonate in 50 ml toluene in a round bottom flask equipped with a Dean-Stark trap was refluxed for 24 hrs. The reaction mixture was poured into ethyl acetate/water mixture and the aqueous layer was extracted with ethyl acetate. The combined organic extracts were washed with water, followed by brine, dried and concentrated. Kugelrohr distillation at 150°–160° C./0.5 mm Hg provided 2.75 g (75%) of an oil.

EXAMPLE 5

Preparation of (R)-3-methyl-4-benzyloxazolidin-2-one 1.67 g of compound obtained under Example 4 in 15 ml of dry DMF was added to 0.5 g of sodium hydride in 20 ml of dry DMF. After the initial reaction had subsided the contents were heated at 60° C. for 1 hour and after cooling to r.t. 2 ml of iodomethane was added. After stirring overnight at r.t. the reaction mixture was poured into 100 ml of water and this was extracted with ether. The organic layers were combined, washed with water, brine, dried and concentrated to give 1.23 g of light yellow crystalline material. Recrystallization from methylene chloride/hexane gave 0.65 g of analytically pure white crystalline solid, m.p. 75°–77° C.

EXAMPLE 6

Preparation of 5-decyloxazolidin-2-one 4.6 g of 1,2-epoxydodecane, 12.2 g of potassium cyanate, 25 ml of DMF, 0.2 g of tetraethylammonium bromide and 1.8 ml of water were stirred and heated at 120°–130° C. for 5 hours. The disappearance of the epoxide was followed by thin layer chromatography (tlc). The cooled reaction mixtre was poured into 200 ml of water and this was extracted with ethyl acetate. The combined organic extracts were washed with water, followed by brine, dried and concentrated to give a solid. Recrystallization from methylene chloride/hexane gave 3.7 g (65.2%) of product, m.p. 86°–87° C.

EXAMPLE 7

Preparation of 3-methyl-5-decyloxazolidin-2-one 0.52 g of compound obtained under Example 6 was treated with 0.12 g of 60% NaH and 1 ml of iodomethane in DMF as described under Example 2. Concentration of ether solution gave 0.33 g of an oil, which slowly solidified, m.p. 42°–44° C.

EXAMPLE 8

Preparation of 5-nonyloxazolidin-2-one 13.8 g of racemic 1-amino-2-undecanol (obtained from reaction of decanal with nitromethane in presence of KF followed bysilylation of nitroalcohol and reduction with LAH) and 6.5 g of ethylene carbonate were heated at approximately 110° C. for 48 hours. The progress of the reaction was followed by tlc. The reaction mixture was worked up as under Example 1 to give 12.74 g (81%) of solid, m.p. 83°–85° C.

EXAMPLE 9

Preparation of 5-decyloxazolidin-2-one

A 250 ml oven dried round bottom flask equipped with a nitrogen side-arm inlet, condenser and a magnetic stirring bar was charged with 100 ml of dry benzene and 8 g of dichlorourethane. To this mixture was added dropwise 8 g of 1-dodecene in 20 ml of benzene and the reaction mixture was refluxed for 24 hours. The cooled reaction mixture was diluted with ether and aqueous sodiumbisulfite. The organic layer was washed repeatedly until negative to aqueous KI solution, then dried and concentrated to give 15.8 g of an oil. This was diluted with 100 ml of isopropylalcohol and refluxed for 6 hours. The solution was concentrated and the resulting oil was recrystallized from hexane to afford 5.63 g (51% overall isolated yield) of product, m.p. 86° C.

EXAMPLE 10

Preparation of 4-decyl-1,3-dioxolan-2-one

A 125 ml round bottom flask equipped with a Dean-Stark trap was charged with 10 g of 1,2-dodecanediol, 7.1 g of diethyl carbonate and 50 ml of benzene. The solution was stirred until homogeneous and then 50 mg of 60% NaH was added. The reaction mixture was refluxed for 6 hours and then concentrated to afford 12.2 g of oil. This was taken up in 100 ml of pet. ether and allowed to crystallize in freezer whereupon 1.1 g of starting diol was recovered. Concentration of the filtrate gave 9.53 g (89.66%) of a colorless oil.

EXAMPLE 11

Preparation of 4,5-dibutoxy-1,3-dimethylimidazolidin-2-one 9 g of 1,3-dimethylurea was added to 15 ml of 40% aqueous glyoxal in 100 ml of 1-butanol. To this stirring solution was added 1 ml of concentrated sulfuric acid and the reaction mixture was allowed to stir overnight at r.t. After dilution with cold water, the reaction mixture was extracted with 3×50 ml of ether. The combined ether extracts were washed with sodium bicarbonate and brine, dried and concentrated to give 20.75 g of a thick oil. Chromatography on silica gel (Ethyl acetate/Hexane) gave 13.63 g (53.7%) of an oil.

EXAMPLE 12

Preparation of 4,5-diethoxy-1-butyl-3-propylimidazolidin-2-one

Example 11 was repeated with 5.14 g of 1-butyl-3-propylurea and 5 ml of 40% aqueous glyoxal in 100 ml of ethanol with 1 ml of conc. sulfuric acid. Work up and silica gel chromatography gave 3.87 g (44%) of an oil.

EXAMPLE 13

Preparation of 4,5-diethoxy-1-octyl-3-propylimidazolidin-2-one

Example 11 was repeated with 10.718 g of 1-octyl-3-propylurea, 9.1 g of 40% aqueous glyoxal, 60 ml of ethanol and 1 ml of conc. sulfuric acid. Work up and silica gel chromatography gave 8.7 g (53%) of an oil.

EXAMPLE 14

Preparation of 4,5-diisopropoxy-1-butyl-3-propylimidazolidin-2-one

Example 11 was repeated with 4.21 g of 1-butyl-3-propylurea, 4 ml of 40% aqueous glyoxal, 80 ml of isopropyl alcohol and 1 ml of conc. sulfuric acid. After work up and silica gel chromatography gave 2.6 g (33%) of an oil.

EXAMPLE 15

Preparation of 4,5-dioctyloxy-1,3-dimethylimidazolidin-2-one 8.93 g of 1,3-dimethylurea, 15 ml of 40% aqueous glyoxal, 50 ml of octanol and 1 ml of conc. sulfuric acid was treated as under Example 11 and gave 10.1 g of an oil.

EXAMPLE 16

Preparation of 3-(3-ethoxypropyl)oxazolidin-2-one

A solution of 15.05 g of 3-ethoxypropylamine and 23 ml of triethylamine in 25 ml of dry benzene was cooled in ice-water bath and a solution of 15 ml of 2-chloroethylchloroformate in 25 ml of dry benzene was added dropwise. The reaction mixture was stirred overnight and the precipitate was filtered, washed with benzene and the filtrate was concentrated to give 30.467 g of an oil. This was taken up in 100 ml of ethanol and was added dropwise to a solution of 3.37 g of sodium in 190 ml of ethanol. After stirring overnight sodium chloride was filtered off, washed with ethanol and the filtrate was concentrated. The residue was taken up in ethyl acetate, washed with water and brine, dried and concentrated. The oil was kugelrohr distilled (125° C./0.5 mm) to give 20.68 g (82.15%) of a colorless oil.

EXAMPLE 17

Preparation of 1-(2-hydroxyethyl)-3-octylimidazolidin-2-one 7.1 g of 3-(2-chloroethyl)oxazolidin-2-one was treated with 12.271 g of octyl amine. The reaction mixture was stirred overnight, diluted with ethyl acetate and washed with water and brine. The organic solution was dried and concentrated to give 9.55 g (83%) of product.

EXAMPLE 18

Preparation of 3-(2-octyloxyethyl)oxazolidin-2-one

To 5.12 g of 60% NaH in 130 ml of THF and 30 ml of DMF was added 12.9 of 3-(2-hydroxyethyl)oxazolidin-2-one and the contents were refluxed for 2 hours. 17 g of 1-bromooctane was added and the reaction mixture was refluxed overnight. It was cooled, poured into water and extracted with ether. The combined organic extracts were dried, concentrated and the residue Was kugelrohr distilled (150°–155° C./0.5 mm) to give 16.87 g (79.6%) of an oil.

EXAMPLE 19

Preparation of 4-undecylimidazolidin-2-one

A dry 250 ml round bottom flask equipped with a nitrogen inlet, reflux condenser and stirring bar was charged with 2.44 g of 5-undecylhydantoin and 100 ml of THF. To this was added dropwise 10 ml of 3.5M Vitride in toluene. After the initial foaming had ceased the reaction mixture was refluxed for 30 hours. The reaction was quenched with saturated sodium sulfate solution and extracted with 3×50 ml of ether. The combined ether extracts were dried, filtered and concentrated. Recrystallization from ether gave 1.8 g (78%) of white crystals, m.p. 97°–99° C.

EXAMPLE 20

Preparation of 3-butyl-4-benzyloxazolidin-2-one

A mixture of 5.005 g of 2-amino-3-phenylpropanol and 3 g of ethylene carbonate in 50 ml of toluene in a round bottom flask with a Dean-Stark trap was refluxed for 48 hours and the reaction was followed by tlc. At the end of the reaction the solution was washed with water and brine and concentrated to dryness to give 5.86 g of light yellow oil. The racemic 4-benzyloxazolidin-2-one was dissolved in 20 ml of THF and was added to 1.98 g of 60% NaH in 40 ml of THF and 10 ml of DMF. After the initial reaction had subsided the reaction mixture was refluxed for 2 hours. After cooling to r.t. 5.44 g of 1-bromobutane in 20 ml of THF was added and the reaction mixture was refluxed overnight. It was then poured into ice-water and extracted twice with ethyl acetate. Combined organic extracts were washed three times with water, followed by brine. After drying, the solution was concentrated to give 7.625 g of crude oil. This was kugelrohr distilled (155°–160° C./0.3 mm) to give 6.54 g (84.7% overall yield) of product.

EXAMPLE 21

Preparation of 1,3-dimethyl-4-undecylimidazolidin-2-one

A dry 250 ml flask was charged with 0.5 g of hexane washed NaH and 40 ml of dry DMF. To this stirring suspension was slowly added 1 g of 4-undecylimidazolidin-2-one (Example 19) in 10 ml of dry DMF. The reaction mixture was heated at 100 C for 2 hours and after cooling 2 ml of iodomethane was injected dropwise. The reaction mixture was stirred for 48 hours at room temperature and then quenched with dilute HCl. The neutralized mixture was extracted with 3×30 ml portions of ethyl acetate. The combined organic extracts were dried and concentrated to give 1.17 g of crude product. Kugelrohr distillation at 135°–140° C./0.1 mm gave 0.82 g (77%) of colorless oil.

EXAMPLE 22

Preparation of 1-butyl-3-(2-ethoxyethyl)imidazolidin2-one 6.17 g of 3-(2-chloroethyl)oxazolidin-2-one and 6.45 g of 1-aminobutane were stirred together for 30 hours at room temperature and then at reflux for 6 hours. The cooled reaction mixture was diluted with water and extracted with ether. The organic extracts were dried and concentrated to give 5.53 g (70%) of crude 1-butyl-3-(2-hydroxyethyl)imidazolidin-2-one. A dry 250 ml flask equipped with nitrogen inlet, refluxcondenser and stirring bar was charged with 1.34 g of hexane washed 60% NaH/oil and 40 ml of dry DMF. To this was slowly added 5.23 g of 1-butyl-3-(2-hydroxyethyl-)imidazolidin-2-one in 10 ml of THF. After the initial reaction had subsided the reaction mixture was heated at 60° C. for 2 hours. 3.1 ml ofiodoethane was injected dropwise into the reaction mixture and it was refluxed for 16 hours. The reaction mixture was cooled and quenched with dilute HCl and ether. The ether layer was washed with brine, dried and concentrated to give 5.15 g (85.5%) of crude product. Kugelrohr distillation at 120°–125° C./0.2 mm gave colorless oil.

EXAMPLE 23

Preparation of 1-(3-ethoxypropyl)-3-(2-methoxyethyl)imidazolidin-2-one

A mixture of 6.5 g of 3-(2-chloroethyl)oxazolidin-2-one, 4.57 g of 3-ethoxypropylamine and 10 g of triethylamine was refluxed for 10 hours, diluted with THF and water. The organic layer was worked up to give 5.13 g of 1-(3-ethoxypropyl)-3-(2-hydroxyethyl-)imidazolidin-2-one, b.p. 110° C./0.5 mm. This material was methylated with 4.26 g of iodomethane and 1.13 g of NaH (60% in oil) in 60 ml of THF as mentioned under Example 22. This gave 3.9 g (71.4%) of oil, b.p. 100°–105° C./0.5 mm.

EXAMPLE 24

Preparation of 3-(1-oxododecyl)oxazolidin-2-one 2.612 g of oxazolidin-2-one in 25 ml of dry chloroform and 4.88 g of dry pyridine was treated with 6.55 g of dodecanoyl chloride in 10 ml of dry chloroform dropwise. After stirring overnight the solution was refluxed for 2 hours. The solution was concentrated to dryness and the residue was taken up in chloroform, washed with dilute acid, water and brine. After drying, the solution was concentrated to give a solid. This was recrystallized from petrol ether to give 5.455 g (67.5%) of a colorless solid, m.p. 66° C.

EXAMPLE 25

Preparation of 3-(oxazolidin-2-onyl)ethyl dodecanoate

A solution of 18.53 g of crude 2-(hydroxyethyl)oxazolidin-2-one and 25 ml of triethylamine in 300 ml of dichloromethane was reacted dropwise with 31.84 g of dodecanoyl chloride. The reaction mixture was stirred overnight at room temperature and quenched with aqueous solution of sodium bicarbonate. The organic layer was washed with water, brine, dried and concentrated to give 33 g (80%) of a solid. Recrystallization from hexane/dichloromethane gave 28 g of white crystals, m.p. 62°–64° C.

EXAMPLE 26

Preparation of cis and trans 2-oxa-4-azabicyclo[10.3.0.]pentadecan-3-one

A solution of 15.7 g cyclododecene and 15.8 g dichlorourethane in 125 ml of benzene was refluxed for 12 hours under a nitrogen atmosphere. The reaction mixture was cooled, diluted with 100 ml of ether and then washed repeatedly with saturated sodiumbisulfite solution. After washing with brine the organic layer was dried and concentrated to give 19.5 g of crudechlorourethane. This was heated at 100°–120° C. for 6 hours. The resulting thick dark oil was diluted with hexane and allowed to stand in the freezer overnight. The solid was filtered and recrystallized from hexane/dichloromethane to give 5.66 g of white crystals, m.p. 84°–86° C. The mother liquor was concentrated to give 5.23 g of thick oil which after flash chromatography (silica gel; ethyl acetate/hexane) gave additional 1.23 g of white crystals, m.p. 85° C. and 0.96 g of a clear oil, which slowly solidified. Recrystallization from hexane gave 0.25 g of crystals, m.p. 72°–74° C.

EXAMPLE 27

Preparation of 4-(dodecanoyloxymethyl)-4-methyloxazolidin-2-one

A solution of 10.5 g of 2-amino-2-methyl-1,3-propanediol and 12.3 g of diethyl carbonate, 0.5 g of sodium ethoxide in 100 ml of toluene was refluxed for 20 hours, cooled and concentrated at reduced pressure to give 13.6 g of crude product. Recrystallization from ethanol gave 9.23 g (67%) of4-hydroxymethyl-4-methyloxazolidin-2-one, m.p. 115 C. To a solution of 2.62 g of 4-hydroxymethyl-4-methyloxazolidin-2-one and 5 ml of triethylamine in 100 ml of dichloromethane was added dropwise 4.6 g of dodecanoyl chloride in 10 ml of dichloromethane. After 3 hours at room temperature the reaction mixture was concentrated, the residue was taken up in ether and washed with aqueous sodium bicarbonate. The ether layer was dried and concentrated to give 4.33 g (69%) of a thick yellow oil. Recrystallization from dichloromethane/hexane (1:10) gave 2.73 g (45%) of white crystals, m.p. 53–55 C.

EXAMPLE 28

Preparation of 4-methyl-4-(octyloxymethyl)oxazolidin-2-one

A 250 ml dry flask, equipped with a nitrogen inlet, reflux condenser and stirring bar was charged with 1.25 g of hexane washed NaH (60% in oil) and 80 ml of dry DMF. To the hydride suspension was added 5 g of 4-hydroxymethyl-4-methyloxazolidin-2-one. The reaction mixture was stirred at r.t. for 30 minutes and then heated for 1 hour at 100 C. 7.3 g of bromooctane was added through a syringe and the reaction mixture was refluxed for overnight. The reaction was worked up as under Example 18 and the organic solution was concentrated. Kugelrohr distillation at 130–140 C/0.1 mm gave 5.44 g (59%) of product.

The compounds of the present invention were tested in vitro as penetration enhancers according to the procedure outlined below.

EXAMPLE 29

Human stratum corneum was isolated from full thickness human skin as described by Bronaugh et al., J. Pharm. Sci. 75, 1094 (1986). The skin was placed between the donor and the receptor compartments of diffusion cells in such a way that the dermal side of the skin faced the receptor compartment which was filled with normal saline (pH 7.2–7.4). The stratum corneum was equilibrated at 37° C. overnight prior to the application of a topical formulation or transdermal patch. All formulations were studied in triplicate.

About 500 mg of the following three Isosorbide Dinitrate (ISDN) formulations (60% ISDN & 40% Lactose) were applied to cover the stratum corneum surface within the donor compartment. The entire contents of the receptor compartment were removed at specific time intervals over 51 hours and replenished with fresh saline. The aliquots were analyzed by HPLC and the average cumulative amount of ISDN in micrograms permeating over the study period was calculated.

The results are shown below.

| Cream Formulation | Average Cumulative Amount of ISDN in Micrograms permeating over 51 hours |
|---|---|
| (1) 1% ISDN (Control) | 759 ± 21 |
| (2) 1% ISDN + 1.4% 1-Dodecyl-hexahydro-2H-azepin-2-one | 709 ± 170 |
| (3) 1% ISDN + 1.4% Compound of Example 1 | 1275 ± 104 |
| (4) 1% ISDN + 1.6% Compound of Example 2 | 1020 ± 69 |
| (5) 10% ISDN (IsoKET* Cream) | 1308 ± 357 |

*ISOKET Cream is a commercially marketed product of Schwarz Pharma GmbH, West Germany.

The results clearly show that compounds of Examples 1 and 2 have superior permeation enhancing properties as compared to control and a known permeation enhancer. The data also indicates that the formulations containing 1% drug with enhancers of this invention are as effective as a commercial formulation with 10% drug.

EXAMPLE 30

The procedure of Example 29 was repeated with the following Hydrocortisone (HC) cream formulations.

| Cream Formulation | Average Cumulative Amount of HC in Micrograms permeating over 24 hours |
|---|---|
| (1) 0.5% HC (Control) | 1.657 ± 0.02 |
| (2) 0.5% HC + 1% Compound of Example 1 | 4.970 ± 0.79 |
| (3) 1% HC (Rx, Commercial product) | 1.528 ± 0.20 |

The results clearly show that the formulation containing compound of Example 1 shows superior permeation as compared to control cream and to a commercial formulation with higher quantity of drug.

EXAMPLE 31

The procedure of Example 29 was repeated with the following Isosorbide Dinitrate (ISDN) formulations incorporated in a transdermal patch.

| Patch Formulation | Average Cumulative Amount of ISDN in Micrograms permeating over 51 hours |
|---|---|
| (1) 3% ISDN (60%); Control | 476 ± 167 |
| (2) 3% ISDN (60%) + 8% Compound of Example 1 | 1438.4 ± 174 |
| (3) 3% ISDN (100%); Control | 702.7 ± 57 |
| (4) 3% ISDN (100%) + 3% Compound of Example 1 | 1355.8 ± 262.5 |

The results clearly establish that the permeation of ISDN from the transdermal patch containing enhancer of Example 1 is superior to the control.

EXAMPLE 32

The procedure of Example 29 was repeated with the following Indomethacin (INDO) gels and creams.

| | Average Cumulative Amount of INDO in Micrograms permeating over 51 hours |
|---|---|
| Gel Formation | |
| (1) 1% INDO (Control) | 304.8 ± 20 |
| (2) 1% INDO + 1% Compound of Example 1 | 370.9 ± 56 |
| Cream Formulation | |
| (1) 1% INDO | 72 ± 9 |
| (2) 1% INDO + 1% Compound of Example 1 | 128 ± 6.1 |

The results clearly show the advantage of incorporating enhancer of Example 1.

EXAMPLE 33

The procedure of Example 29 was repeated with Morphine Sulfate (MS) formulations incorporated in a transdermal patch.

| Patch Formulation | Average Cumulative Amount of MS in Micrograms permeating over 51 hours |
|---|---|
| (1) 5% MS (Control) | 354 ± 76 |
| (2) 5% MS + 1% Compound of Example 1 | 622 ± 81.6 |

The results show the superiority of the transdermal patch formulation containing enhancer of Example 1.

EXAMPLE 34

The procedure of Example 29 was repeated with Progesterone (PG) incorporated in transdermal patch formulations. The releasing media contained 30% ethanol in normal saline.

| Patch Formulation | Average Cumulative Amount of PG in Micrograms permeating over 51 hours |
|---|---|
| (1) 3% PG (Control) | 86 ± 61 |
| (2) 3% PG + 5% Compound of Example 1 | 434 ± 135 |

The results clearly show the superiority of the transdermal patch containing enhancer of Example 1.

EXAMPLE 35

The procedure of Example 29 was repeated with the following Diltiazem hydrochloride (DZ) cream formulation.

| Cream Formulation | Average Cumulative amount of DZ in Micrograms permeating over 24 hours |
|---|---|
| (1) 5% DZ (Control) | 125.3 ± 37 |
| (2) 5% DZ + 3% Compound of Example 1 | 303.0 ± 79.1 |

The results clearly show that incorporation of penetration enhancer of Example 1 in the formulation improves the permeation of Diltiazem hydrochloride through the skin significantly over the control.

EXAMPLE 36

The procedure of Example 29 was repeated with the following Nicotine Cream and Patch Formulations.

| | Average Cumulative Amount of Nicotine in Micrograms permeating over 51 hours |
|---|---|
| Cream Formulation | |
| (1) 1% Nicotine (Control) | 1541.0 ± 98.0 |
| (2) 1% Nicotine + 3% Compound of Example 1 | 2002.0 ± 74.0 |
| (3) 5% Nicotine (Control) | 5908.0 ± 257.5 |
| (4) 5% Nicotine + 3% Compound of Example 1 | 8497.2 ± 1195 |
| Patch Formulation | |
| (1) 5% Nicotine (Control) | 154.6 ± 27.8 |
| (2) 5% Nicotine + 3% Compound of Example 1 | 208.1 ± 23.6 |
| (3) 10% Nicotine (Control) | 2865.4 ± 96.0 |
| (4) 10% Nicotine + 3% Compound of Example 1 | 3520.0 ± 139.0 |

The results clearly show that Compound of Example 1, when incorporated with Nicotine in a cream and a patch formulation, enhances the permeation significantly over control.

EXAMPLE 37

Example 29 was repeated with the following Isosorbide Dinitrate (ISDN) cream formulations.
The results are shown below.

| Cream formulation | Average Cumulative Amount of ISDN in Micrograms permeating over 51 hours |
|---|---|
| (1) 1% ISDN (Control) | 897.2 ± 70.7 |
| (2) 1% ISDN + 1% Compound of Example 19 | 1318.4 ± 21.6 |
| (3) 1% ISDN + 1% Compound of Example 21 | 1257.0 ± 137.0 |
| (4) 1% ISDN + 1% Compound of Example 10 | 1174.5 ± 37.2 |
| (5) 1% ISDN + 1% Compound of Example 16 | 1110.9 ± 84.1 |
| (6) 1% ISDN + 1% Compound of Example 18 | 1185.1 ± 94.7 |
| (7) 1% ISDN + 1% Compound of Example 22 | 1091.2 ± 125.0 |
| (8) 1% ISDN + 1% Compound of Example 20 | 1147.7 ± 36.0 |
| (9) 1% ISDN + 1% Compound of Example 12 | 1057.7 ± 12.0 |
| (10) 1% ISDN + 1% Compound of Example 15 | 1175.6 ± 33.6 |

These results demonstrate clearly that Compounds of Examples 19, 21, 10, 16, 18, 22, 20, 12 and 15, when incorporated in a formulation, have superior permeation enhancing properties as compared to control.

EXAMPLE 38

The Indomethacin (INDO) gel formulation used in Example 32 was prepared as follows.

| | % |
|---|---|
| Indomethacin | 1.0 |
| Carbopol 941 | 2.0 |
| Diisopropanolamine | 2.0 |
| 95% Ethanol | 50.0 |
| Diisopropyl adipate | 5.0 |
| 4-Decyloxazolidin-2-one | 1.0 |
| Deionized water q.s. | 100.0 |

EXAMPLE 39

The following solution formulation is prepared.

| | Solution % |
|---|---|
| Griseofulvin | 1 |
| 4-Decyloxazolidin-2-one | 1 |
| Isopropyl myristate | 5 |
| Fragrance | 0.1 |
| Ethanol | 92.9 |

This formulation is effective in the treatment of fungus infections.

EXAMPLE 40

An aerosol form of the formulation of Example 39 is prepared by preparing the following mixture:

| Formulation of Example 39 | 25% |
|---|---|
| Freon[1] | 75%[1] |

[1] Freon is 75/25 Freon 114/12

EXAMPLE 41

The following cream formulation is prepared:

| | % |
|---|---|
| Clindamycin base | 1.0 |
| Stearyl Alcohol, U.S.P. | 12.0 |
| Ethoxylated Cholesterol | 0.3 |
| Synthetic spermaceti | 7.5 |
| Sorbitan monooleate | 1.0 |
| Polysorbate 80, U.S.P. | 3.0 |
| 4-Decyloxazolidin-2-one | 1.0 |
| Sorbitol solution, U.S.P. | 5.5 |
| Sodium citrate | 0.5 |
| Chemoderm #844 | 0.2 |
| Purified water | 68.0 |

This formulation is effective in the treatment of acne.

EXAMPLE 42

The following solution formulation is prepared:

|  | % |
|---|---|
| Neomycin sulfate | 0.5 |
| Lidocaine | 0.5 |
| Hydrocortisone | 0.25 |
| 4-Decyloxazolidin-2-one | 1.0 |
| Propylene glycol | 97.75 |

This solution is effective for the treatment of otitis in domestic animals.

EXAMPLE 43

The following sunscreen emulsion is prepared:

|  | % |
|---|---|
| PABA | 2.0 |
| Benzyl alcohol | 0.5 |
| 4-Decyloxazolidin-2-one | 1.0 |
| Polyethylene glycol | 10.0 |
| Isopropyl lanolate | 3.0 |
| Lantrol | 1.0 |
| Acetylated lanolin | 0.5 |
| C12–C15 benzoate | 5.0 |
| Diisopropyl adipate | 2.0 |
| Cetyl alcohol | 1.0 |
| Veegum | 1.0 |
| Propylene glycol | 3.0 |
| Purified water | 70.0 |

EXAMPLE 44

The following antineoplastic solution is prepared:

|  | % |
|---|---|
| 5-Fluorouracil | 5.0 |
| 4-Decyloxazolidin-2-one | 1.5 |
| Polyethylene glycol | 5.0 |
| Purified water | 88.5 |

EXAMPLE 45

The following insect repellant atomizing spray is prepared:

|  | % |
|---|---|
| N,N-diethyltoluamide | 1.0 |
| 4-Decyloxazolidin-2-one | 1.0 |
| Ethanol | 98.0 |

EXAMPLE 46

The following cream formulation may be prepared containing about 0.001 to 1%, with preferably 0.1% Fluocinolone acetonide:

|  | % |
|---|---|
| Oil Phase |  |
| Fluocinolone acetonide | 0.1 |
| 4-Decyloxazolidin-2-one | 1.6 |
| Cetyl alcohol | 9.3 |
| Stearyl alcohol | 1.3 |
| Glycerol monostearate | 3.8 |
| Water Phase |  |
| Propylene glycol | 10.0 |
| Sodium dodecyl sulfate | 0.1 |
| Deionized water q.s. | 100.0 |

The steroid is dissolved in the vehicle and added to a stirred, cooling melt of the other ingredients. The preparation is particularly useful for the treatment of inflamed dermatoses by topical application to the affected skin area. The amount and frequency of application is in accordance with standard practice for topical application of this steroid. Penetration of this steroid in the inflamed tissue is enhanced and a therapeutic level is achieved more rapidly and sustained for longer duration than when the steroid is applied in the conventional formulation.

EXAMPLE 47

The following skin moisturizing formulation is prepared:

|  | % |
|---|---|
| Na Pyrrolidone-5-carboxylate | 1.5 |
| Glycerine | 5.0 |
| Citric acid | 0.035 |
| Na citrate | 0.055 |
| Allantoin | 0.2 |
| Ethanol, 95% | 9.0 |
| Oleth-15 | 1.11 |
| Linoleic acid | 1.0 |
| 4-decyloxazolidin-2-one | 2.0 |
| Octyldimethyl PABA | 0.1 |
| Water | 80.0 |

EXAMPLE 48

Example 38-47 are repeated, except the 4-decyloxazolidin-2-one, is replaced with an equal amount of each of the following listed compounds and comparable results are obtained.

(1) 3-methyl-4-oxazolidin-2-one
(2) 3-butyl-4-benzyloxazolidin-2-one
(3) 5-decyloxazolidin-2-one
(4) 3-methyl-5-decyloxazolidin-2-one
(5) 5-decyltetrahydro-1,3-oxazin-2-one
(6) 3-methyl-5-decyltetrahydro-1,3-oxazin-2-one
(7) 4-undecylimidazolidin-2-one
(8) 1,3-dimethyl-4-undecylimidazolidin-2-one
(9) 3-(2-octyloxyethyl)oxazolidin-2-one
(10) 1-butyl-3-(2-ethoxyethyl)imidazolidin-2-one
(11) 3-(3-ethoxypropyl)oxazolidin-2-one
(12) 4,5-diethoxy-1-butyl-3-propylimidazolidin-2-one
(13) 4,5-dioctyloxy-1,3-dimethylimidazolidin-2-one
(14) 4,5-dioctyloxyimidazolidin-2-one
(15) 1-(3-ethoxypropyl)-3-(2-methoxyethyl)imid azolidin-2-one
(16) 3-(1-oxododecyl)oxazolidin-2-one
(17) 3-(oxazolidin-2-onyl)ethyl dodecanoate
(18) 4-methyl-4-(octyloxymethyl)oxazolidin-2-one
(19) 4-(dodecanoyloxymethyl)-4-methyloxazolidin-2-one
(20) 5-(octyloxymethyl)oxazolidin-2-one
(21) 3-methyl-5-(octyloxymethyl)oxazolidin-2-one
(22) 3-methyl-5-(octanoyloxymethyl)oxazolidin-2-one
(23) 4-decyl-1-3-dioxolan-2-one
(24) 4-[(decyloxy)methyl]-1,3-dioxolan-2-one
(25) 4-[(decyloxy)methyl]-1,3-dioxolan-2-one In summary, the invention comprises compositions and methods of enhancing the penetration of physiologically active compounds, the principal such compounds being pharmaceuticals, through the skin or membranes of animals generally, and humans in particular, and agricultural methods of treating plants, comprising the dermal or membrane application of compositions consisting essentially of physiologically and biologically active compounds in intimate mixture with one or more compounds of the formula

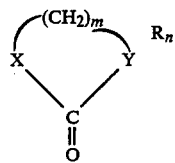

where:
R=H, Alkyl group containing from 1-18 carbon atoms, cycloalkyl, aryl, aralkyl, alkoxy, hydroxyalkyl, alkoyloxyalkyl, acyloxyalkyl and alkoxyalkyl;
X=O and $NR_1$, where $R_1$ is selected from H, alkyl, aralkyl, acyl group containing from 1-18 carbon atoms, cycloalkyl, hydroxyalkyl, alkoyloxyalkyl acyloxyalkyl and alkoxyalkyl;
Y=O and $NR_2$, where $R_2$ is selected from H, alkyl, aralkyl, cycloalkyl, acyl group containing from 1-18 carbon atoms, hydroxyalkyl, alkoyloxyalkyl, acyloxyalkyl and alkoxyalkyl;
m=2-4; and
n=0-4.
with the provisos that:
(i) when R=H, X=$NR_1$, and Y=$NR_2$ then $R_1$ and $R_2$ are not alkyl;
(ii) when R=H, X=O and Y=$NR_2$, then $R_2$ is not alkyl; and
(iii) when X and Y are O, then R is not lower alkyl, i.e., if alkyl, R is C5-C18.

As will be clearly apparent, there is no criticallity as to the nature of the physiologically active compound or compounds the penetration of which may be enhanced by the method and compositions of this invention, the criticallity lying in the use of penetration enhancers as defined.

Quantities and ratios of the constitutents of the composition are, likewise, not critical. The inclusion of other constituents in the composition of such natures and ratios as do not significantly reduce the penetration enhancement resulting from the defined penetration enhancers is contemplated; indeed, the present invention greatly enhances the effectiveness of pharacetical and other physiologically active preparations, e.g. cosmetic preparations, when the defined penetration enhancing compounds are an effective constituent in compositions which include both physiologically active compounds and carriers and/or diluents which are commonly used to add bulk or volume to increase the surface area of the dermis which can be treated, to control the concentration of or dosage of the pharmaceutical or other physiologically active compound, or simply for convenient handling. For example, in some applications a predetermined microgram quantity of a pharmaceutical carried by or intimately mixed with the defined penetration enhancers may be applied to the skin of the user as a small dot on an adhesive patch while in other applications compositions within the scope of this invention may be applied by spraying, spreading or otherwise applying thousands of gallons of a given composition to plants, fields or even larger geographic areas to enhance penetration of the physiologically active material into plants, insects, animals, etc. either to enhance, retard or prevent growth, as may be the effect of the physiologically active material.

What constitutes an effective amount of the defined enhancers depends upon the what constituent of the compositions of this invention is used as the reference and the condition of the composition at the time the amount is determined or calculated. In the examples mentioned, the enhancer may comprise 90% or 99% or more of the small dot of composition on the patch if the physiologically active material is very potent or may comprise parts per million of an agricultural spray. Thus, an effective amount is that amount which is associated with the physiologically active compound(s) at the time of application to the dermis and which amout signficantly enhances the penetration or the associated physiologically active compound(s). Thus, while it not possible precisely to define what in every instance constitutes an effective amount or ratio or percentage of the enhancers of this invention in a composition, in general the enhancers comprise about 0.1 volume percent or more of penetration compositions at the time penetration of the physiologically active compound(s) occurs.

While particular embodiments of the invention have been described it will be understood of course that the invention is not limited thereto since many obvious modifications can be made and it is intended to include within this invention any such modifications as will fall within the scope of appended claims.

INDUSTRIAL APPLICATION

The present invention is useful in medicine, research, agriculture and in the health care and cosmetic industries generally.

I claim:
1. A composition useful for treating of humans or other animals by the application to the skin or other membrane of such animal, such composition comprising of one or more physiologically active compounds in intimate mixture with an effective amount of one or more penetration enhancers having the formula:

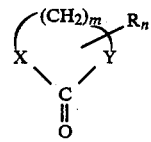

where:
R=H, Alkyl group containing from 1-18 carbon atoms, cycloalkyl, aryl, aralkyl, alkoxy, hydroxyalkyl, alkoyloxyalkyl, acyloxyalkyl and alkoxyalkyl;
X=O and $NR_1$, where $R_1$ is selected from H, alkyl, aralkyl, acyl group containing from 1-18 carbon atoms, cyloalkyl, hydroxyalkyl, alkoyloxyalkyl, acyloxyalkyl and alkoxyalkyl;
Y=O and $NR_2$, where $R_2$ is selected from H, alkyl, aralkyl, cycloalkyl, acyl group containing from 1-18 carbon atoms, hydroxyalkyl, alkoyloxyalkyl, acyloxyalkyl and alkoxyalkyl;
m=2-4; and
n=0-4.
with the provisos that:

(i) at least one of X and Y is O;
(ii) when R=H, X=O and Y=NR$_2$, then R$_2$ is not alkyl; and
(iii) when X and Y are O, then R is not lower alkyl, i.e., if alkyl, R is C5-C18.

2. The composition of claim 1 wherein the physiologically active compound is pharmaceutically active in animal therapy and the penetration enhancer is an oxazolidin-2-one selected from the group consisting of:
4-decyloxazolidin-2-one,
3-methyl-4-decyloxazolidin-2-one,
3-acetyl-4-decyloxazolidin-2-one,
4-benzyloxazolidin-2-one,
3-methyl-4-benzyloxazolidin-2-one,
3-butyl-4-benzyloxazolidin-2-one,
3-(2-butyl)-4-benzyloxazolidin-2-one,
3-(2-methylpropyl)-4-benzyloxazolidin-2-one,
5-decyloxazolidin-2-one,
3-methyl-5-decyloxazolidin-2-one,
3-acetyl-5-decyloxazolidin-2-one,
4,4-dimethyl-5-decyloxazolidin-2-one,
3,4,4-trimethyl-5-decyloxazolidin-2-one,
3-acetyl-4,4-dimethyl-5-decyloxazolidin-2-one,
4-phenyloxazolidin-2-one,
3-methyl-4-phenyloxazolidin-2-one,
3-acetyl-4-phenyloxazolidin-2-one,
4-methyl-5-phenyloxazolidin-2-one,
3,4-dimethyl-5-phenyloxazolidin-2-one,
3-acetyl-4-methyl-5-phenyloxazolidin-2-one,
3-(1-oxododecyl)oxazolidin-2-one,
3-(1-oxododecyl)-4-methyloxazolidin-2-one,
3-(1-oxododecyl)-5-methyloxazolidin-2-one,
3-(1-oxododecyl)-4,4-dimethyloxazolidin-2-one,
3-(1-oxodecyl)-4-(2-propyl)oxazolidin-2-one,
3-(1-oxodecyl)-4-(2-butyl)oxazolidin-2-one,
3-(1-oxodecyl)-4-benzyloxazolidin-2-one,
3-(1-oxooctadec-9-enyl)oxazolidin-2-one,
3-(1-oxooctadec-9-enyl)-4,4-dimethyloxazolidin-2-one,
3-(2-hydroxyethyl)-4-decyloxazolidin-2-one,
3-(2-ethoxyethyl)-4-decyloxazolidin-2-one,
3-(3-ethoxypropyl)oxazolidin-2-one,
3-(2-octyloxyethyl)oxazolidin-2-one,
3-(2-oxazolidonyl) ethyl dodecanoate
5-(octyloxy methyl) oxazolidin-2-one,
3-methyl-5-(hexyloxy methyl) oxazolidin-2-one,
3-methyl-5-(octanoyloxy) oxazolidin-2-one,
4-methyl-4-(octyloxymethyl) oxazolidin-2-one, and
4-(dodecanoyloxymethyl)-4-methyloxazolidin-2-one.

3. The composition of claim 1 wherein the physiologically active compound is pharmaceutically active in animal therapy and the penetration enhancer is an oxazin-2-one selected from the group consisting of:
5-decyltetrahydro-1,3-oxazin-2-one,
3-methyl-5-decyltetrahydro-1,3-oxazin-2-one,
3-acetyl-5-decyltetrahydro-1,3-oxazin-2-one,
4-dodecyltetrahydro-1,3-oxazin-2-one,
3-methyl-4-dodecyltetrahydro-1,3-oxazin-2-one,
3-acetyl-4-dodecyltetrahydro-1,3-oxazin-2-one, and
3(1-oxododecyl)tetrahydro-1,3-oxazin-2-one.

4. The composition of claim 1 wherein the physiologically active compound is pharmaceutically active in animal therapy and the penetration enhancer is a dioxolan-2-one selected from the group consisting of:
4-decyl-1,3-dioxolan-2-one,
4-decyloxymethyl-1,3-dioxolan-2-one, and
4[(octadec-9-enoyloxy) methyl]-1,3-dioxolan-2-one.

5. A method of treating humans and other animals comprising applying to the skin or other membrane of the animal to be treated one or more physiologically active compounds in intimate mixture with an effective amount of one or more penetration enhancers having the formula:

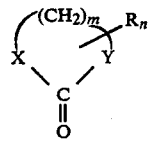

where:
R=H, Alkyl group containing from 1-18 carbon atoms, cycloalkyl, aryl, aralkyl, alkoxy, hydroxyalkyl, alkoyloxyalkyl, acyloxyalkyl and alkoxyalkyl;
X=O and NR$_1$, where R$_1$ is selected from H, alkyl, aralkyl, acyl group containing from 1-18 carbon atoms, cycloalkyl, hydroxyalkyl, alkoyloxyalkyl, acyloxyalkyl and alkoxyalkyl;
Y=O and NR$_2$, where R$_2$ is selected from H, alkyl, aralkyl, cycloalkyl, acyl group containing from 1-18 carbon atoms, hydroxyalkyl, alkoyloxyalkyl, acyloxyalkyl and alkoxyalkyl;
m=2-4; and
n=0-4.
with the provisos that:
(i) at least one of X and Y is O;
(ii) when R=H, X=O and Y=NR$_2$, then R is not alkyl; and
(iii) when X and Y are O, then R is not lower alkyl, i.e., if alkyl, R is C5-C18.

6. The method of claim 5 wherein the physiologically active compound is pharmaceutically active in animal therapy and is applied to the dermis of an animal and the penetration enhancer is an oxazolidin-2-one selected from the group consisting of:
4-decyloxazolidin-2-one,
3-methyl-4-decyloxazolidin-2-one,
3-acetyl-4-decyloxazolidin-2-one,
4-benzyloxazolidin-2-one,
3-methyl-4-benzyloxazolidin-2-one,
3-butyl-4-benzyloxazolidin-2-one,
3-(2-butyl)-4-benzyloxazolidin-2-one,
3-(2-methylpropyl)-4-benzyloxazolidin-2-one,
5-decyloxazolidin-2-one,
3-methyl-5-decyloxazolidin-2-one,
3-acetyl-5-decyloxazolidin-2-one,
4,4-dimethyl-5-decyloxazolidin-2-one,
3,4,4-trimethyl-5-decyloxazolidin-2-one,
3-acetyl-4,4-dimethyl-5-decyloxazolidin-2-one,
4-phenyloxazolidin-2-one,
3-methyl-4-phenyloxazolidin-2-one,
3-acetyl-4-phenyloxazolidin-2-one,
4-methyl-5-phenyloxazolidin-2-one,
3,4-dimethyl-5-phenyloxazolidin-2-one,
3-acetyl-4-methyl-5-phenyloxazolidin-2-one,
3-(1-oxododecyl)oxazolidin-2-one,
3-(1-oxododecyl)-4-methyloxazolidin-2-one,
3-(1-oxododecyl)-5-methyloxazolidin-2-one,
3-(1-oxododecyl)-4,4-dimethyloxazolidin-2-one,
3-(1-oxodecyl)-4-(2-propyl)oxazolidin-2-one,
3-(1-oxodecyl)-4-(2-butyl)oxazolidin-2-one,
3-(1-oxodecyl)-4-benzyloxazolidin-2-one,
3-(1-oxooctadec-9-enyl)oxazolidin-2-one, 3-(1-oxooctadec-9-enyl)-4,4-dimethyloxazolidin-2-one,
3-(2-hydroxyethyl)-4-decyloxazolidin-2-one,
3-(2-ethoxyethyl)-4-decyloxazolidin-2-one,
3-(3-(3-ethoxypropyl)oxazolidin-2-one,
3-(2-octyloxyethyl)oxazolidin-2-one,
3-(2-oxazolidonyl) ethyl dodecanoate
5-(octyloxy methyl) oxazolidin-2-one,
3-methyl-5-(hexyloxy methyl) oxazolidin-2-one,
3-methyl-5-(octanoyloxy) oxazolidin-2-one,
4-methyl-4-(octyloxymethyl) oxazolidin-2-one, and
4-(dodecanoyloxymethyl)-4-methyloxazolidin-2-one.

7. The method of claim 5 wherein the physiologically active compound is pharmaceutically active in animal therapy and is applied to the dermis of an animal and the penetration enhancer is an oxazin-2-one selected from the group consisting of:
5-decyltetrahydro-1,3-oxazin-2-one,
3-methyl-5-decyltetrahydro-1,3-oxazin-2-one,
3acetyl-5-decyltetrahydro-1,3-oxazin-2-one,
4dodecyltetrahydro-1,3-oxazin-2-one,
3-methyl-4-dodecyltetrahydro-1,3-oxazin-2-one,
3-acetyl-4-dodecyltetrahydro-1,3-oxazin-2-one, and
3-(1-oxododecyl)tetrahydro-1,3-oxazin-2-one.

8. The method of claim 5 wherein the physiologically active compound is pharmaceutically active in animal therapy and is applied to the dermis of an animal and the penetration enhancer is a dioxolan-2-one selected from the group consisting of:
4-decyl-1,3-dioxolan-2-one,
4-decyloxymethyl-1,3-dioxolan-2-one, and
4[(octadec-9-enoyloxy) methyl]-1,3-dioxolan-2-one.

* * * * *